United States Patent
Jupiter et al.

(10) Patent No.: US 7,643,604 B2
(45) Date of Patent: Jan. 5, 2010

(54) STATIONARY INSPECTION SYSTEM FOR THREE-DIMENSIONAL IMAGING EMPLOYING ELECTRONIC MODULATION OF SPECTRAL DATA FROM COMPTON-SCATTERED GAMMAS

(76) Inventors: Clyde P. Jupiter, 265 Amberleigh Dr., Silver Spring, MD (US) 20905; Nenad N. Kondic, 2212 Greenhills Dr., Valrico, FL (US) 33596

( * ) Notice: Subject to any disclaimer, the term of this patent is extended or adjusted under 35 U.S.C. 154(b) by 0 days.

(21) Appl. No.: 12/189,762

(22) Filed: Aug. 11, 2008

(65) Prior Publication Data

US 2009/0060119 A1 Mar. 5, 2009

Related U.S. Application Data

(63) Continuation-in-part of application No. 10/373,112, filed on Feb. 26, 2003, now Pat. No. 7,412,022.

(60) Provisional application No. 60/360,012, filed on Feb. 28, 2002.

(51) Int. Cl.
*G01N 23/00* (2006.01)
*G01T 1/00* (2006.01)
*G01T 1/16* (2006.01)
*G01B 15/00* (2006.01)

(52) U.S. Cl. .............. 378/2; 378/62; 378/69; 378/82; 378/87; 250/363.06

(58) Field of Classification Search ............ 378/2, 378/62, 63, 80–82, 86–89; 250/363.06
See application file for complete search history.

(56) References Cited

U.S. PATENT DOCUMENTS

| | | | | |
|---|---|---|---|---|
| 3,748,470 A | * | 7/1973 | Barrett | 378/2 |
| 3,860,821 A | * | 1/1975 | Barrett | 250/363.01 |
| 3,936,639 A | * | 2/1976 | Barrett | 250/369 |
| 4,015,135 A | * | 3/1977 | Tipton, Jr. | 250/574 |
| 4,017,730 A | * | 4/1977 | Barrett | 250/363.06 |
| 4,075,483 A | * | 2/1978 | Tancrell et al. | 250/363.06 |
| 4,158,770 A | * | 6/1979 | Davis et al. | 378/2 |
| 4,241,404 A | * | 12/1980 | Lux | 378/2 |
| 4,345,153 A | * | 8/1982 | Yin | 250/369 |
| 4,360,797 A | * | 11/1982 | Fenimore et al. | 382/278 |
| 4,448,529 A | * | 5/1984 | Krause | 356/310 |
| 4,506,374 A | * | 3/1985 | Flynn | 378/2 |
| 5,173,928 A | * | 12/1992 | Momose et al. | 378/4 |
| 5,512,754 A | * | 4/1996 | Enos | 250/363.1 |
| 5,717,733 A | * | 2/1998 | Kurbatov et al. | 378/71 |
| 5,866,907 A | * | 2/1999 | Drukier et al. | 250/366 |
| 5,960,057 A | * | 9/1999 | Majewski et al. | 378/62 |
| 6,169,287 B1 | * | 1/2001 | Warburton | 250/370.1 |
| 6,510,197 B1 | * | 1/2003 | Mitchell et al. | 378/62 |
| 2001/0038681 A1 | * | 11/2001 | Stanton et al. | 378/55 |

* cited by examiner

*Primary Examiner*—Edward J Glick
*Assistant Examiner*—Anastasia Midkiff
(74) *Attorney, Agent, or Firm*—Doster Greene, LLC

(57) ABSTRACT

An inspection system according to various embodiments can include a stationary mono-energetic gamma source and a detector-spectrometer. The detector-spectrometer is configured to employ a modulation of energy bin boundaries within a multi-channel pulse height analyzer to encode voxels within the inspected object, and apply an analysis to determine the three-dimensional density image of the inspected object.

10 Claims, 20 Drawing Sheets

FIG 1. Measurement System 100

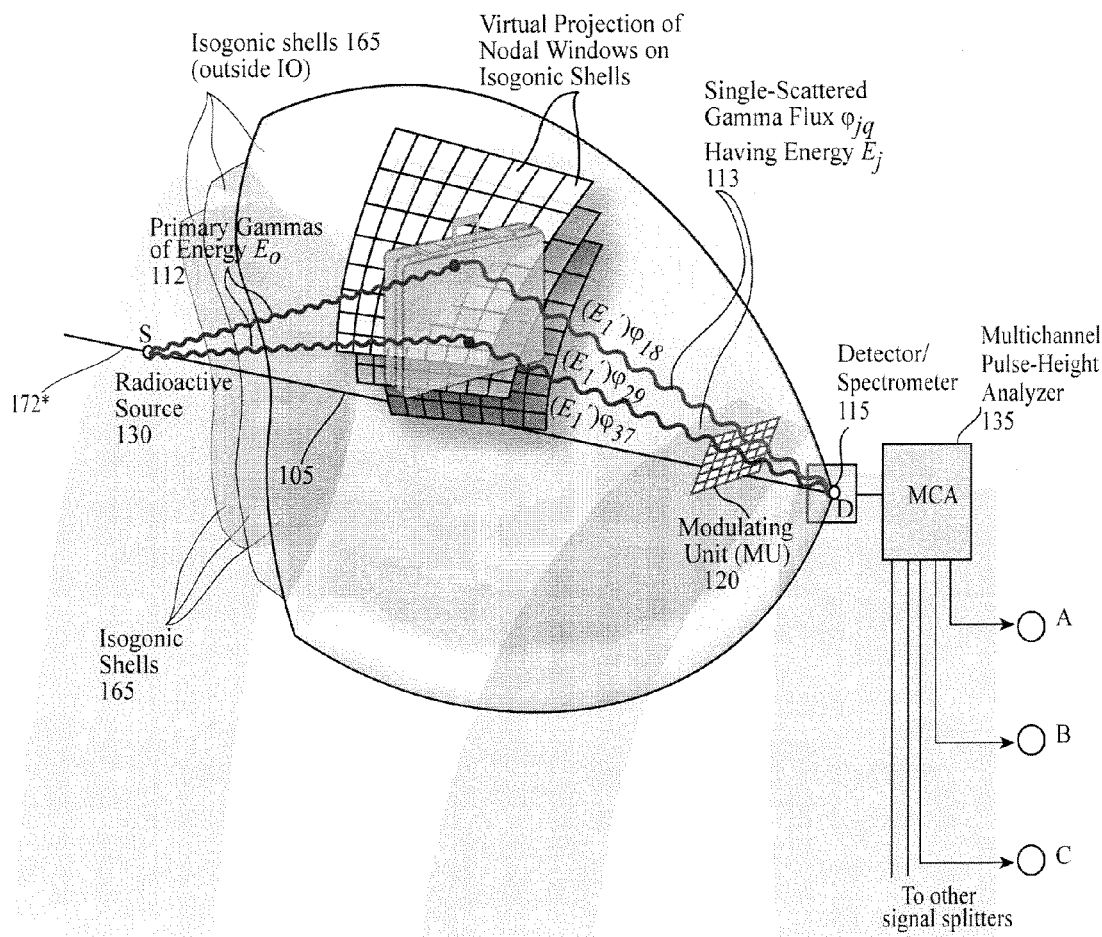

| Step 1 | Step 2 | Step 3 | Step 4 | Step 5 |
|---|---|---|---|---|
| Irradiation of the inspected object (IO), using mono-energetic gamma photons having constant flux intensity and energy $E_o$ from an isotopic source. | Single-scattered gamma flux $\varphi_{jq}$ having energy $E_j{'}$, emanating from the virtual isogonic slice #$j$ in the IO. The energy $E_j{'}$ (with $1 \leq j \leq J$) of scattered gamma photons is a function of the scattering angle $\theta_j$, and is determined by the Compton formula. | Modulation of gamma fluxes $\varphi_{jq}$ with a time-varying attenuation function $a(q,t)$, showing the rectangular configuration of the MU, with $I \cdot K = N$ nodal windows (NWs). | Modulated gamma fluxes exit the MU with a time-variance characterized by $\varphi_{jq} \cdot a(q,t)$. Since for each $j$ value, $q_{max} = N$, there are $N$ such time-dependent fluxes, each of them modulated in a NW-specific manner. | Gammas are detected by D and sorted into $J$ energy bins within the MCA. The time-variation $a(q,t)$ of each $j^{th}$ portion of the gamma flux is preserved in the MCA output signals $D_j(t)$ which differ (with different values of $j$) among themselves. |

For $n = 1$, $\sigma_{j1} = (T)\{[\Phi_{j1}(A_1'B_1'+A_1'B_1'')] + [\Phi_{j2}(A_2'B_1'+A_2'B_1'')] + \ldots + [\Phi_{jq}(A_q'B_1'+A_q'B_1'')] + \ldots + [\Phi_{jN}(A_N'B_1'+A_N'B_1'')]\}$ $\underbrace{\phantom{XX}}_{C_{11}} \quad \underbrace{\phantom{XX}}_{C_{12}} \quad \underbrace{\phantom{XX}}_{C_{1q}} \quad \underbrace{\phantom{XX}}_{C_{1N}}$ For $n = 2$, $\sigma_{j2} = (T)\{[\Phi_{j1}(A_1'B_2'+A_1'B_2'')] + [\Phi_{j2}(A_2'B_2'+A_2'B_2'')] + \ldots + [\Phi_{jq}(A_q'B_2'+A_q'B_2'')] + \ldots + [\Phi_{jN}(A_N'B_2'+A_N'B_2'')]\}$ $\underbrace{\phantom{XX}}_{C_{21}} \quad \underbrace{\phantom{XX}}_{C_{22}} \quad \underbrace{\phantom{XX}}_{C_{2q}} \quad \underbrace{\phantom{XX}}_{C_{2N}}$ For $n = n$, $\sigma_{jn} = (T)\{[\Phi_{j1}(A_1'B_n'+A_1'B_n'')] + [\Phi_{j2}(A_2'B_n'+A_2'B_n'')] + \ldots + [\Phi_{jq}(A_q'B_n'+A_q'B_n'')] + \ldots + [\Phi_{jN}(A_N'B_n'+A_N'B_n'')]\}$ $\underbrace{\phantom{XX}}_{C_{n1}} \quad \underbrace{\phantom{XX}}_{C_{n2}} \quad \underbrace{\phantom{XX}}_{C_{nq}} \quad \underbrace{\phantom{XX}}_{C_{nN}}$ For $n = N$, $\sigma_{jN} = (T)\{[\Phi_{j1}(A_1'B_N'+A_1'B_N'')] + [\Phi_{j2}(A_2'B_N'+A_2'B_N'')] + \ldots + [\Phi_{jq}(A_q'B_N'+A_q'B_N'')] + \ldots + [\Phi_{jN}(A_N'B_N'+A_N'B_N'')]\}$ $\underbrace{\phantom{XX}}_{C_{N1}} \quad \underbrace{\phantom{XX}}_{C_{N2}} \quad \underbrace{\phantom{XX}}_{C_{Nq}} \quad \underbrace{\phantom{XX}}_{C_{NN}}$

STATIONARY INSPECTION SYSTEM FOR THREE-DIMENSIONAL IMAGING EMPLOYING ELECTRONIC MODULATION OF SPECTRAL DATA FROM COMPTON-SCATTERED GAMMAS

REFERENCE TO RELATED APPLICATION

This application is a continuation-in-part of U.S. patent application Ser. No. 10/373,112, filed on Feb. 26, 2003, now U.S. Pat. No. 7,412,022 and claims benefit of U.S. Provisional Patent Application No. 60/360,012, filed Feb. 28, 2002, the contents of both of which are incorporated in their entirety herein by reference.

BACKGROUND OF THE INVENTION

1. Field of the Invention

This invention relates to systems and methods employing the encoding of scattered gamma fluxes for determining three-dimensional density distributions within an object or body to identify the presence of contraband within the object, or to identify internal characteristics within the object or body, or to detect medical abnormalities in a human body.

2. Description of the Related Art

There is a recognized and growing need for improved capability to "see" inside closed boundaries of objects and for accurate measurement of their internal characteristics. For instance, inspection devices are needed to examine baggage and containers to enhance security and search for contraband at airports, government facilities, public buildings, and other possible targets of terrorism. Inspection devices can be installed at check points to scan baggage and other types of containers so that their contents can be characterized and inspected for contraband such as explosives, weapons, drugs and other illicit substances. Non-invasive inspection devices have also become an important tool for on-line monitoring of characteristics of materials undergoing industrial processing within tanks and pipes.

In the medical field, inspection devices, especially non-invasive devices, provide many life-saving benefits. They are used by physicians and medical personnel to assist with the diagnosis and treatment of medical abnormalities in a human body and to mitigate the need for expensive and risky surgical procedures.

Imaging inspection systems have evolved from simple X-ray imaging systems providing two-dimensional images, to more sophisticated automated systems capable of three-dimensional imaging. Such current devices and techniques include Computer Assisted Tomography (CAT), Positron-Electron Emission Tomography (PET), and Magnetic Resonance Imaging (MRI). However, these conventional devices and techniques generally rely on multiple sources and/or complex arrays of detectors, and require a relative scanning motion between the inspected object and the principal system components. Such operating conditions result in significant complexity, size, cost, inspection time, and radiation exposure. A need exists for faster baggage-screening devices having good imaging capabilities to detect and identify contraband; detection machines are needed that search and accurately detect a wider range of contraband including non-metal weapons explosives and components of weapons of mass destruction; further, a need exists for cheaper and smaller inspection devices.

SUMMARY

The present invention may satisfy one or more of the above-mentioned desirable features. Other features and/or advantages may become apparent from the description which follows.

A three-dimensional image-generating device according to various embodiments can include an external gamma radiation source configured to irradiate an inspected object with source gamma rays to generate a three-dimensional representation of the inspected object. A radiation detector may be configured to detect Compton-scattered gamma rays scattered from within said inspected object, wherein the radiation detector comprises a gamma spectrometer and approximates a point detector; wherein the gamma spectrometer is configured to register a plurality of single detection events of said Compton-scattered gamma rays; wherein the plurality of single detection events are detected individually; and wherein the gamma spectrometer is configured to concurrently measure energies of Compton-scattered gamma photons associated with said detection events. A multi-channel pulse height analyzer may be coupled to the gamma spectrometer and configured to analyze voltage pulse heights representing the energies of the Compton-scattered gamma photons and sort the voltage pulse heights based upon the energies of the Compton-scattered gamma photons, into a plurality of energy bins. The gamma spectrometer and the multi-channel pulse-height analyzer may be configured to determine a bin-average value of energy for the Compton-scattered gamma rays having a predetermined energy bin width. The gamma spectrometer may be configured to determine values of the gamma count rate for the Compton-scattered gamma rays arriving at the detector, wherein predetermined energy bin widths are established for counted gamma rays having particular specific energies. The multi-channel pulse height analyzer may be configured to assign the bin-average value of energy for each Compton-scattered photon whose energy is associated with a specific isogonic arc having a specific radius. The multi-channel pulse height analyzer may be configured to determine energy bin boundaries for each energy bin such that each energy bin is represented by a first isogonic arc having a first radius and a second isogonic arc having a second radius, wherein the first radius is less than the second radius. The multi-channel pulse height analyzer may be configured to determine the energy bin widths and to represent a virtual two-dimensional space between the first isogonic arc and the second isogonic arc and having an inter-arc strip configuration.

An inspection system according to various embodiments can include a stationary mono-energetic gamma source and a detector-spectrometer. The detector-spectrometer is configured to determine a three-dimensional density image of an inspected object, employ a modulation of energy bin boundaries within a multi-channel pulse height analyzer to encode voxels within the inspected object, and apply an analysis to reconstruct the three-dimensional image of the inspected object.

BRIEF DESCRIPTION OF THE DRAWINGS

FIG. 10A-10B illustrate operational flowcharts according to a method of the invention;

FIG. 11 is a system of equations (Eqs. 15) for solving a set of linear algebraic equations according to an embodiment of the invention;

DETAILED DESCRIPTION OF THE PREFERRED EMBODIMENTS

The Inspection System

Figure 1:
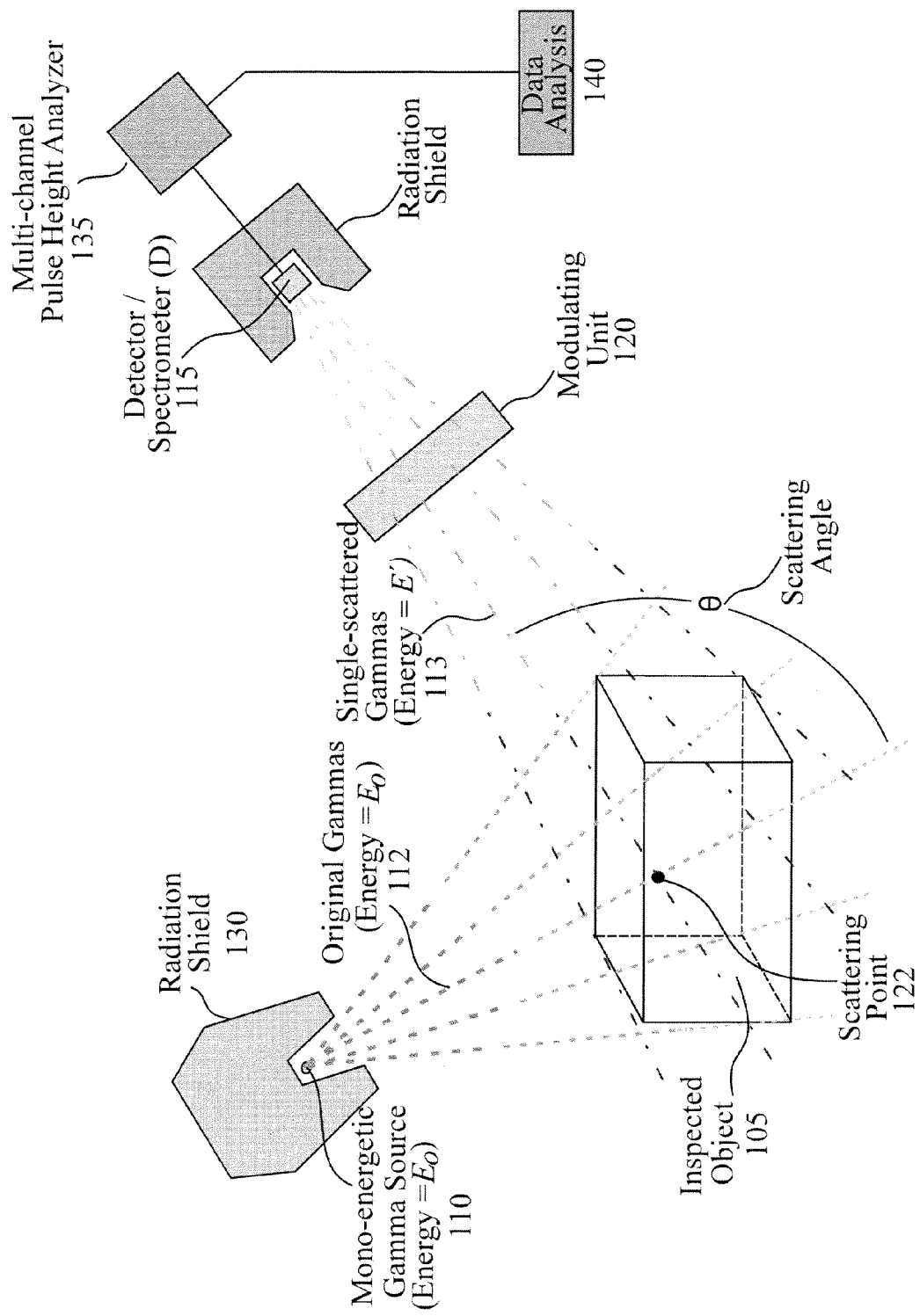
FIG. 1 depicts an inspection system according to an embodiment of the invention.

The invention, as illustrated in FIG. 1, provides a straightforward, non-invasive, rapid, and economic method for imaging an unknown volumetric density distribution within an object with opaque boundaries. The invention may be implemented by detecting and analyzing gamma rays (or X-rays) scattered from an inspected object 105, which is irradiated, for example, by a mono-energetic gamma source 110. The measurement system 100 may include a gamma radiation source 110, radiation detector 115 functioning as a gamma spectrometer, and a modulating unit 120, which may be located between inspected object 105 and detector 115, as shown, or alternately between source 110 and inspected object 105. Alternatively, the gamma radiation source 110, the radiation detector 115, and the modulating unit 120, each may be configured as a single, stationary component of the inspection system. All three of these measurement system components may also have a fixed orientation, and may be positioned on the same side or on opposite sides of the inspected object 105.

Gamma flux transmitted from the mono-energetic source 110 irradiates inspected object 105 and interacts with the object 105, which may cause a measurable fraction of scattered gammas generated within the inspected object 105 to travel from inspected object 105 to detector 115. The scattered gamma stream 113, which is the number of gamma photons passing through NWs within the modulator, is attenuated according to a periodic function (such as a sine or cosine function) by the modulating unit 120. This modulation acts effectively as an encoding process that tags those single-scattered gamma rays 113 that reach detector 115 after interacting with the material within the inspected object 105, or within a pre-selected region of the inspected object 105. The measurement system 100 also utilizes the energy-angle relationship of the Compton scattering process, as discussed below. This Compton energy-angle relationship, coupled with the encoding and decoding of the gamma rays scattered from inspected object 105 and passing through modulating unit 120, enables the reconstruction of the three-dimensional density distribution within inspected object 105.

One of the many features provided by the invention is the design and application of a gamma modulation unit to tag components of the areal distribution of gamma flux across any cross section of the gamma stream, after the gamma rays are scattered from inspected object 105. To enable the invention to locate scattering points within the inspected object 105, the invention may utilize the modulation unit 120 to determine the two-dimensional distribution of scattered gamma flux within inspected object 105. Conjunctively, the invention utilizes the Compton energy-angle relationship for scattered gamma rays to determine a third coordinate thereby identifying each scattering point in three-dimensional space. With the identification of all three coordinates, and measurement of the intensity of scattered gamma flux, a reconstruction of the three-dimensional gamma flux distribution and corresponding mass density distribution in inspected object 105 may be realized.

For personnel safety and to reduce background radiation, source 110 may be shielded in the lateral and rear directions by a radiation shield 130. The radiation detector 115, which may also be stationary, may record single-scattered gamma rays 113 that are projected from inspected object 105 after the original gamma rays 112 from the source interact with atoms within inspected object 105. Detector 115 is a gamma spectrometer that can register a high count rate of single detection events (i.e., single gamma photons). A multi-channel pulse height analyzer 135 (MCA) and a data analysis unit 140, sorts the detection events according to the energy of the detected gamma photon, by registering the energy spectrum of all scattered gamma photons detected by the detector 115 within a specified time period.

Modulating unit 120 imposes a periodic time-dependent attenuation on the otherwise constant incident flux of the gammas as the scattered gamma rays 113 pass through modulating unit 120 on their way to detector 115. While FIG. 1 shows the modulating unit 120 located between inspected object 105 and detector 115, in an alternative embodiment which is not shown, modulating unit 120 may be placed between source 110 and inspected object 105. In this alternate embodiment, modulating unit 120 periodically attenuates the original gamma rays from the source as the gamma rays travel toward inspected object 105. In the embodiment, as shown in FIG. 1, where modulating unit 120 is located between inspected object 105 and detector 115, the modulating unit's cross-sectional area may be oriented perpendicular to the mean direction of the gamma flux of the scattered gamma rays incident upon detector 115. Alternatively, in situations where the modulating unit 120 is positioned between radiation source 110 and inspected object 105, the modulating unit's cross-sectional area may be oriented perpendicular to the mean direction of gamma rays from source 110 incident on the inspected object 105.

Figure 6:
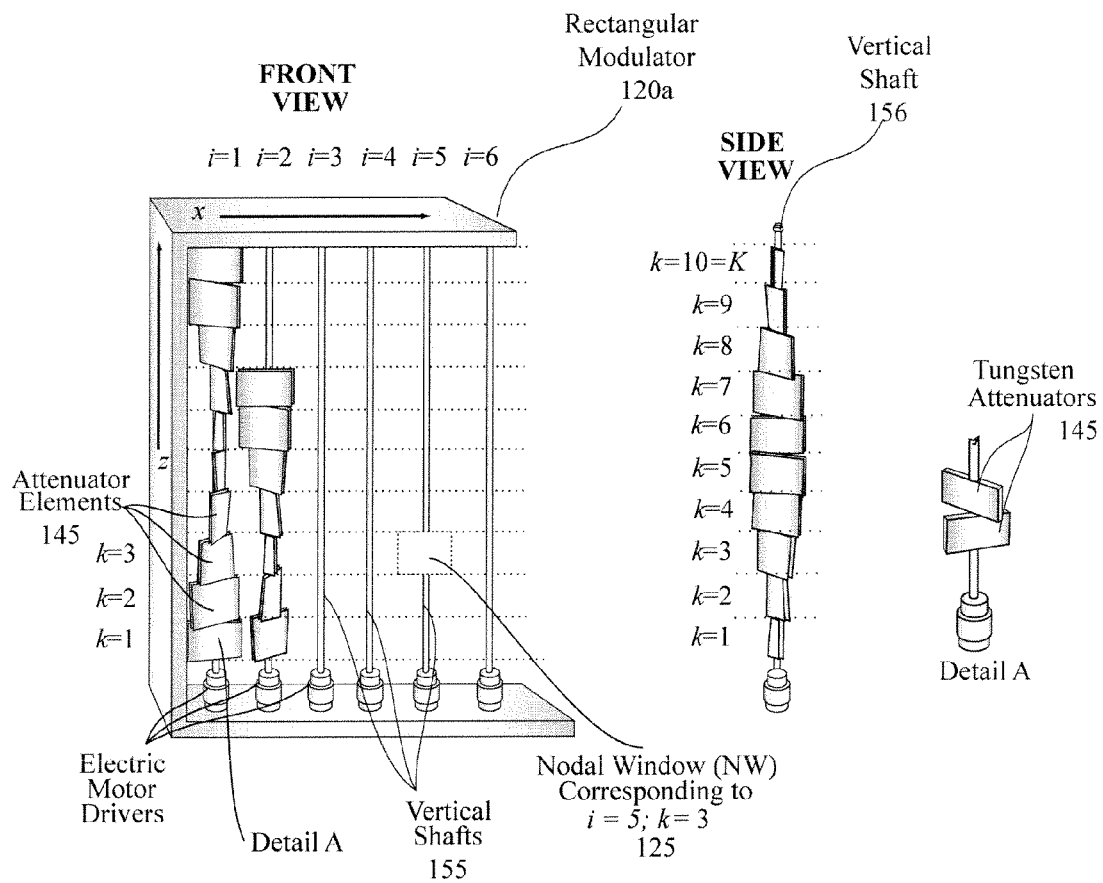
FIG. 6 depicts a rectangular modulating unit designed for rotary oscillation of rectangular gamma attenuating elements according to an embodiment of the invention.
Figure 7:
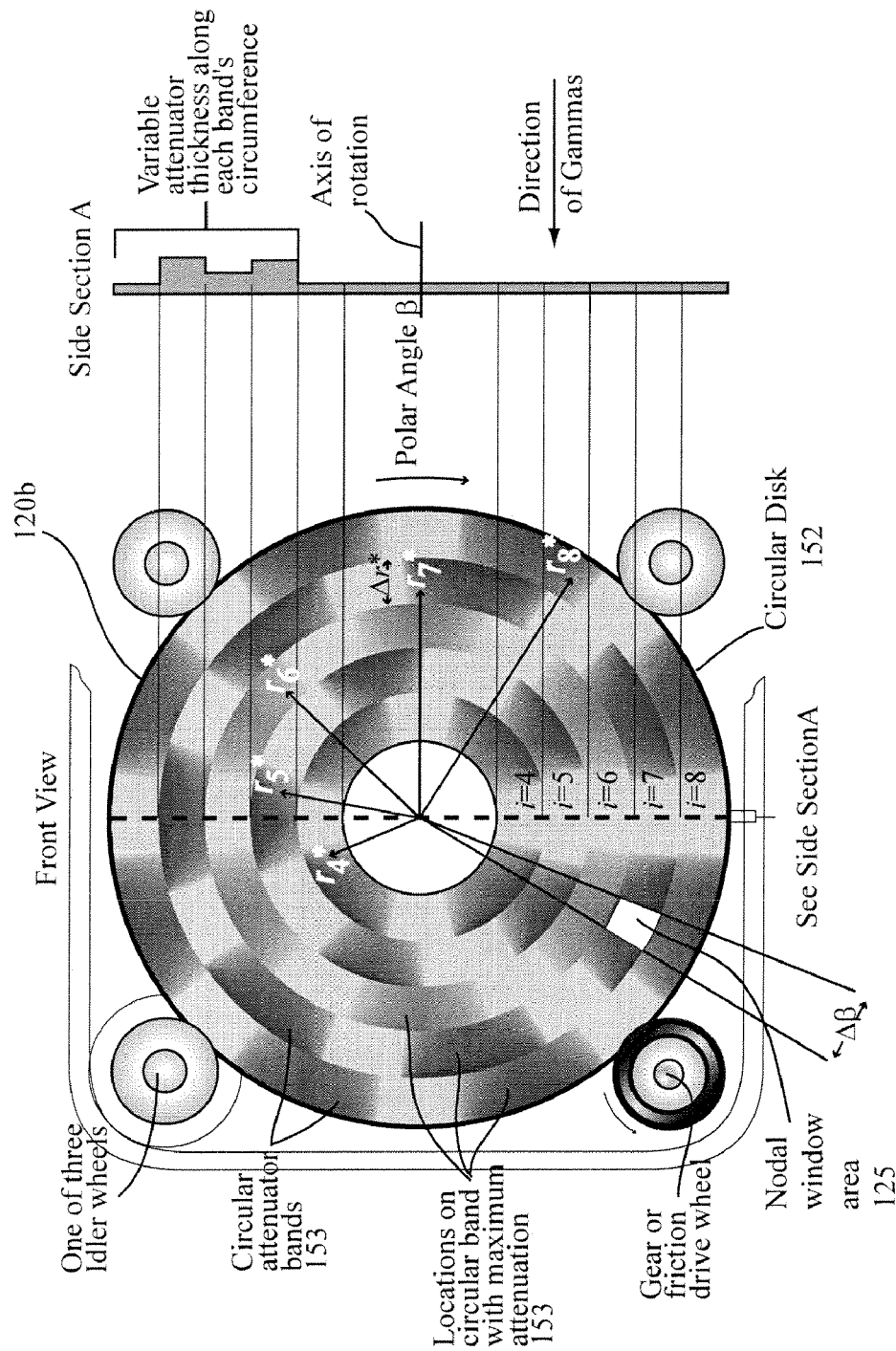
FIG. 7 illustrates a polar modulating unit including attenuator elements consisting of a circular disk with concentric circular tungsten bands of varying thickness according to an embodiment of the invention.
Figure 8:
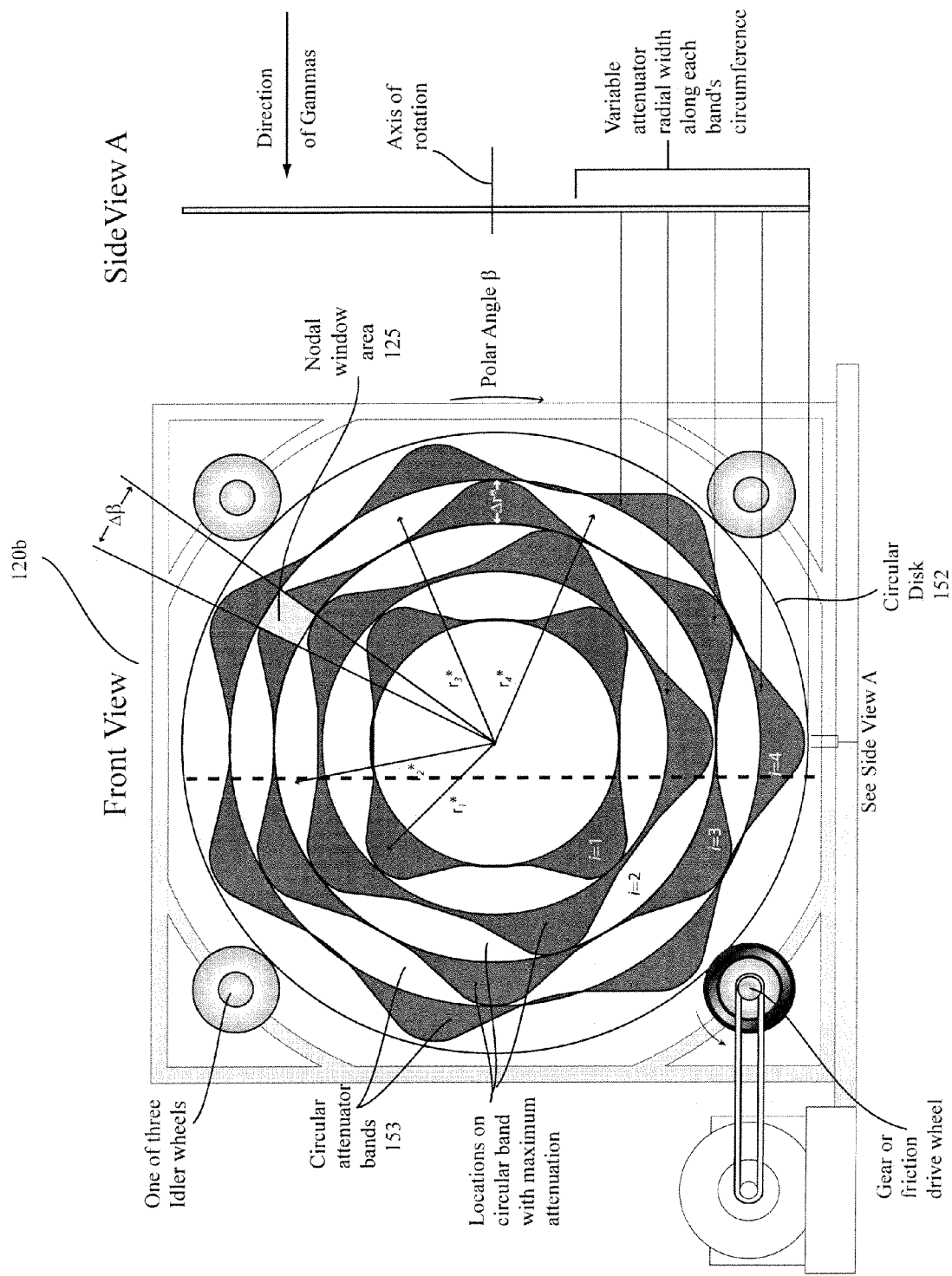
FIG. 8 illustrates a polar modulating unit including tungsten attenuator elements consisting of concentric circular bands of constant thickness and varying widths according to an alternate embodiment of the invention.

Modulating unit 120 may be further configured to include a plurality of NWs 125, as shown in FIGS. 6-8. As the scattered gamma rays 113 encounter the modulating unit 120 (FIG. 1) and pass through the NWs 125, modulating unit 120 imparts a unique time-varying attenuation on the gamma flux (i.e., gamma stream intensity) in each of the NWs as the scattered gamma rays exit each window 125. The time-dependent changes imposed upon the gamma flux transmission may vary with the position of each window in the areal cross-section of modulating unit 120. This time-dependent feature helps to enable a determination of the locations of the scattering points and the values of the gamma fluxes traveling from these scattering points within the corresponding sections of inspected object 105, through the modulating unit 120, and incident on the detector 115.

Dimensions of the inspection system's components, their relative positions, and processing of data can be adjusted to optimize measurements for a wide range of sizes and shapes of inspected objects.

Figure 2:
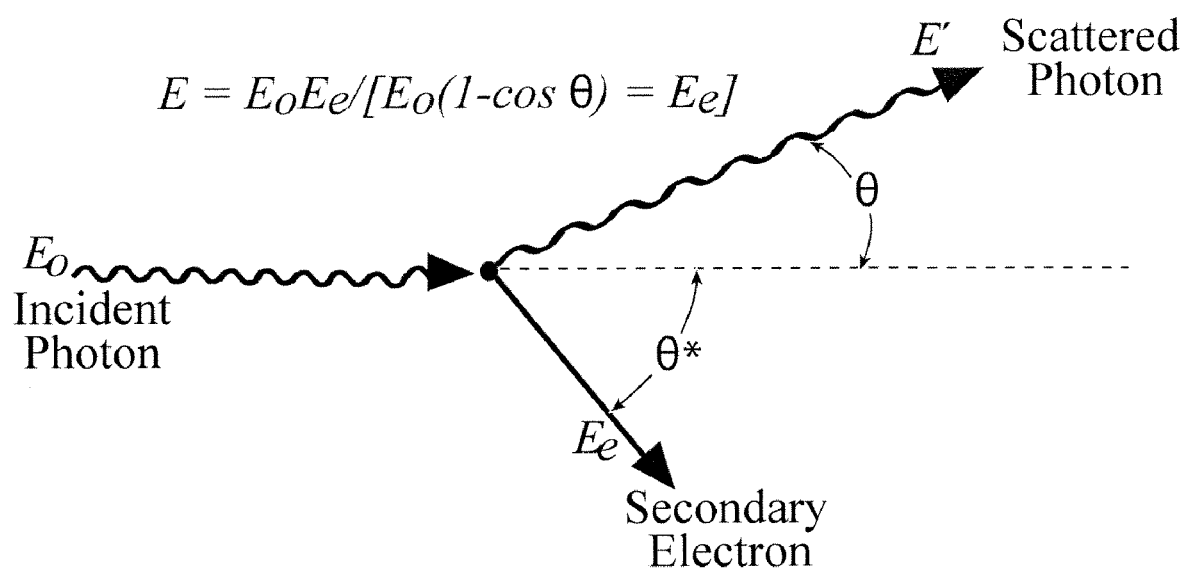
FIG. 2 shows an energy-angle relationship for Compton scattering of X-rays or gamma photons which may be employed in an embodiment of the invention.
Figure 3A:
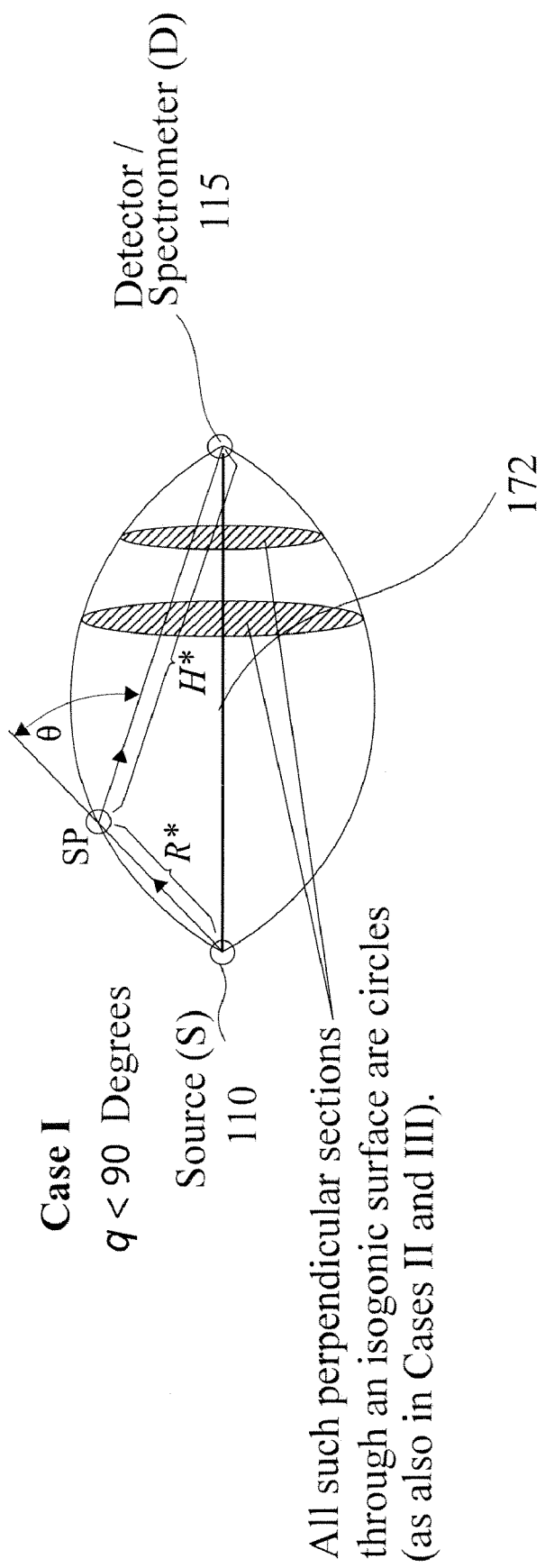
FIGS. 3A-3C illustrate configurations of isogonic surfaces and volumes which may be employed in an embodiment of the invention.
Figure 3B:
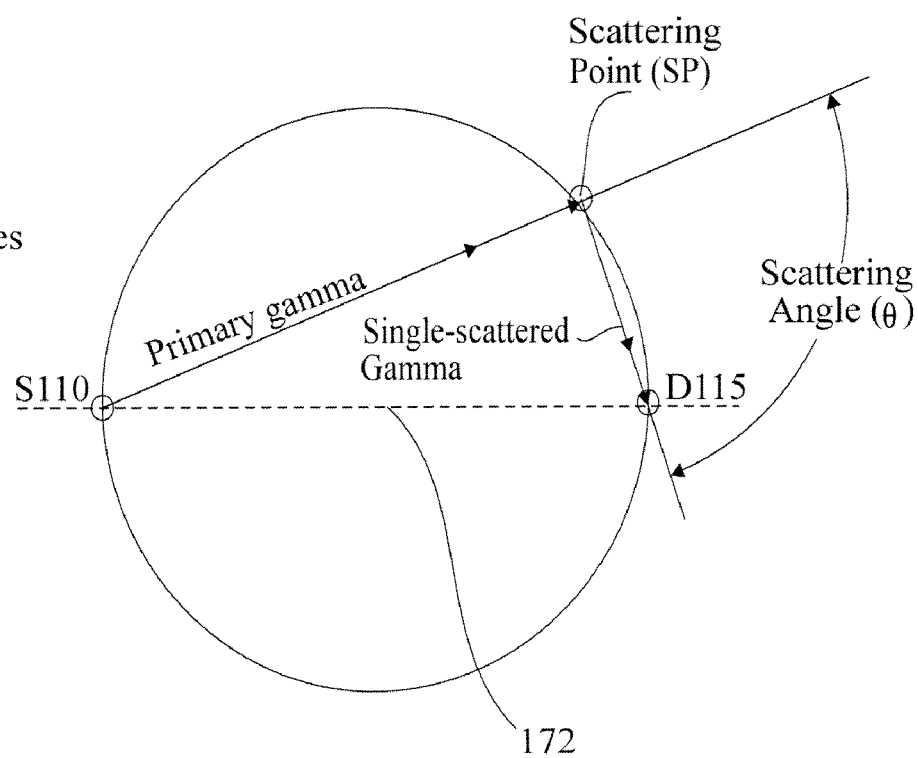
Figure 3C:
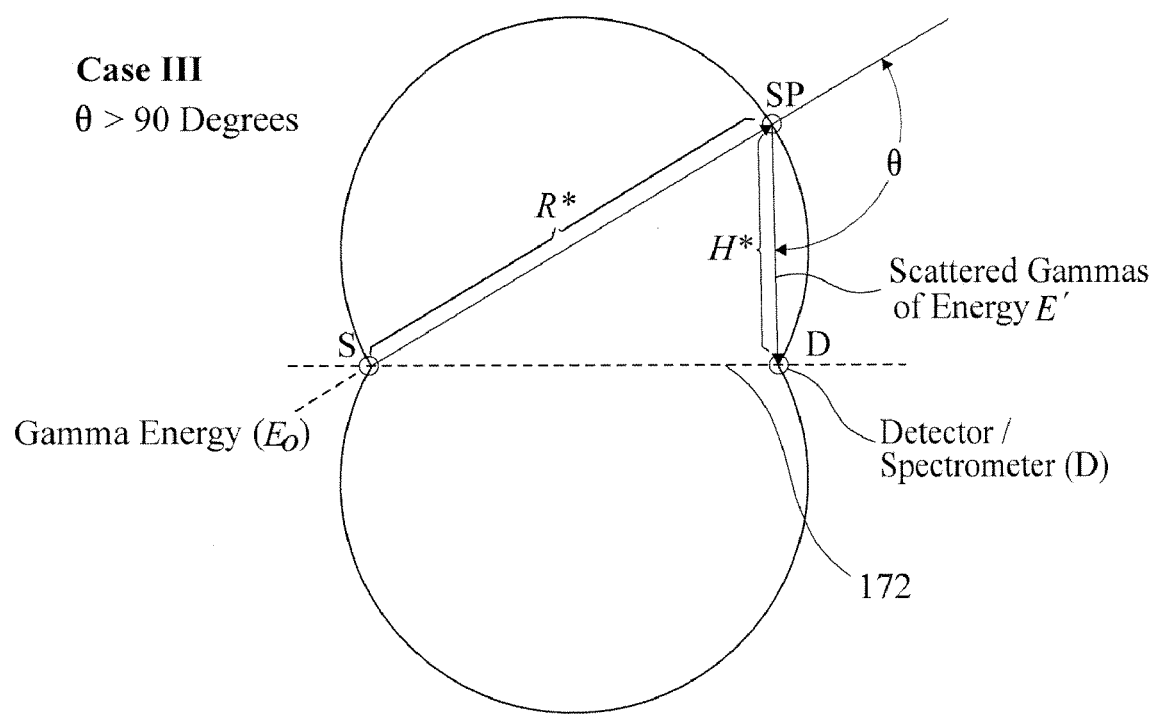

The invention provides several features and benefits. One such feature is that the invention provides a three-dimensional extension of the Compton-scattering geometry, which includes the functional and physical coupling among a gamma source, a scattering point (SP) 122 within an inspected object, and a detector. FIG. 2 illustrates the energy-angle relationship for Compton scattering of X-rays or gamma photons. Here, a primary gamma photon of energy $E_0$ interacts with an atomic electron to yield a secondary gamma photon scattered at an angle θ from the original direction and having a reduced energy E'. A secondary electron is scattered at an angle θ* to conserve momentum. The Compton energy-angle relationship for scattering of gamma photons results in a recognition that a scattering point (SP) 122 located on a circular arc passing through the source 110 and the detector 115, may be situated at any other point on that circular arc without changing the scattering angle (FIGS. 3A-3C). Rotation of this "isogonic" (equal angle) arc about the chord that connects the source 110 and the detector 115 results in a virtual isogonic surface, anywhere on which the scattering point 122 may be located and yield the same angle of scattering (and thereby, scattered photons having the same energy). The portion of these virtual surfaces within the inspected object constitutes "isogonic slices," which may be utilized in the analysis of scattered gammas and identification of their origins. The modulator unit 120 may produce a designated periodic sine or cosine time-variant attenuation of the gamma flux distribution throughout the cross-section of the gamma stream incident upon the modulator unit to encode the flux of the gamma rays in every NW of the modulating unit. The gamma flux encoding provided by the modulating unit 120 enables the identification of the point of origin of gamma rays, which have undergone scattering in the inspected object, and are discriminated by the detector (based upon their measured energy) from other gamma rays arriving at the detector from other isogonic slices. Utilizing gamma rays transmitted from a single mono-energetic source and measured by a single detector spectrometer, the invention also provides a method for simultaneous spatial-encoding, which may be performed by the modulating unit, and energy-encoding of Compton-scattered gamma flux traveling from the inspected object to the detector. A Fourier transform analysis may be included in the decoding process to analyze the measured detector count rates, thus enabling a determination of the three-dimensional distribution of scattering points and corresponding three-dimensional mass density distribution within a stationary inspected object irradiated by mono-energetic gammas.

As a more detailed description of the components shown in FIG. 1, the radiation source 110 can be any radioactive isotope emitting mono-energetic gammas having energies, for example, in the range of approximately a few hundred KeV to the MeV range. The radiation source 110 may be, for example, cesium-137, which emits mono-energetic gamma rays having energy of 661 KeV or sodium-22, emitting gamma photons at 1.27 MeV. Alternatively, in addition to the use of isotopic sources, the gamma radiation source may be any generator of mono-energetic gamma photons. Radiation source 110 may be stationary and housed in a radiation shield 130. During the measurement, the radiation shield 130 may include an opening on one side to permit gamma radiation to stream out in a conical solid angle large enough to irradiate a portion or the entire inspected object 105. When selecting the strength of the source to be used in a particular application, factors such as the desired inspection time, size, density, distance, and geometry of the inspected object may be considered.

Another physical attribute that may be considered in configuring the invention is that the lateral dimensions of the radiation source may be selected to be significantly smaller in comparison to the linear dimensions of the overall inspection system and the inspected object. If, in this example, the size of the inspected object and the distance of the inspected object from the source are more than two orders of magnitude larger than the size of the radiation source, the radiation source can be approximated by a point source, which will simplify the mathematical analysis, as discussed below.

The Modulating Unit

The gamma flux modulating unit 120, as shown in FIGS. 1, 4, 6, 7, and 8, incorporates time-dependent gamma attenuators 145 placed in the path of the scattered gamma flux 113 traveling from inspected object 105 to detector 115 (or alternatively, from the radiation source 110 to inspected object 105). Each gamma attenuator 145 functions as an attenuating element of its associated NW 125. The modulating unit 120 is configured to encode each individual solid angle segment of the gamma flux before the gamma flux arrives at detector 115. Subsequently, the resulting signals are subjected to further processing. The encoding by modulating unit 120 provides a unique time-varying tag at any moment in real time during which the gamma rays 113 pass through the modulating unit 120. Modulating unit 120 acts upon either the original or scattered gamma rays, depending upon the location of the modulating unit, in order to encode the gamma flux and thereby assist in a simultaneous determination of the spatial origin and flux intensity of the scattered gammas.

Figure 4:
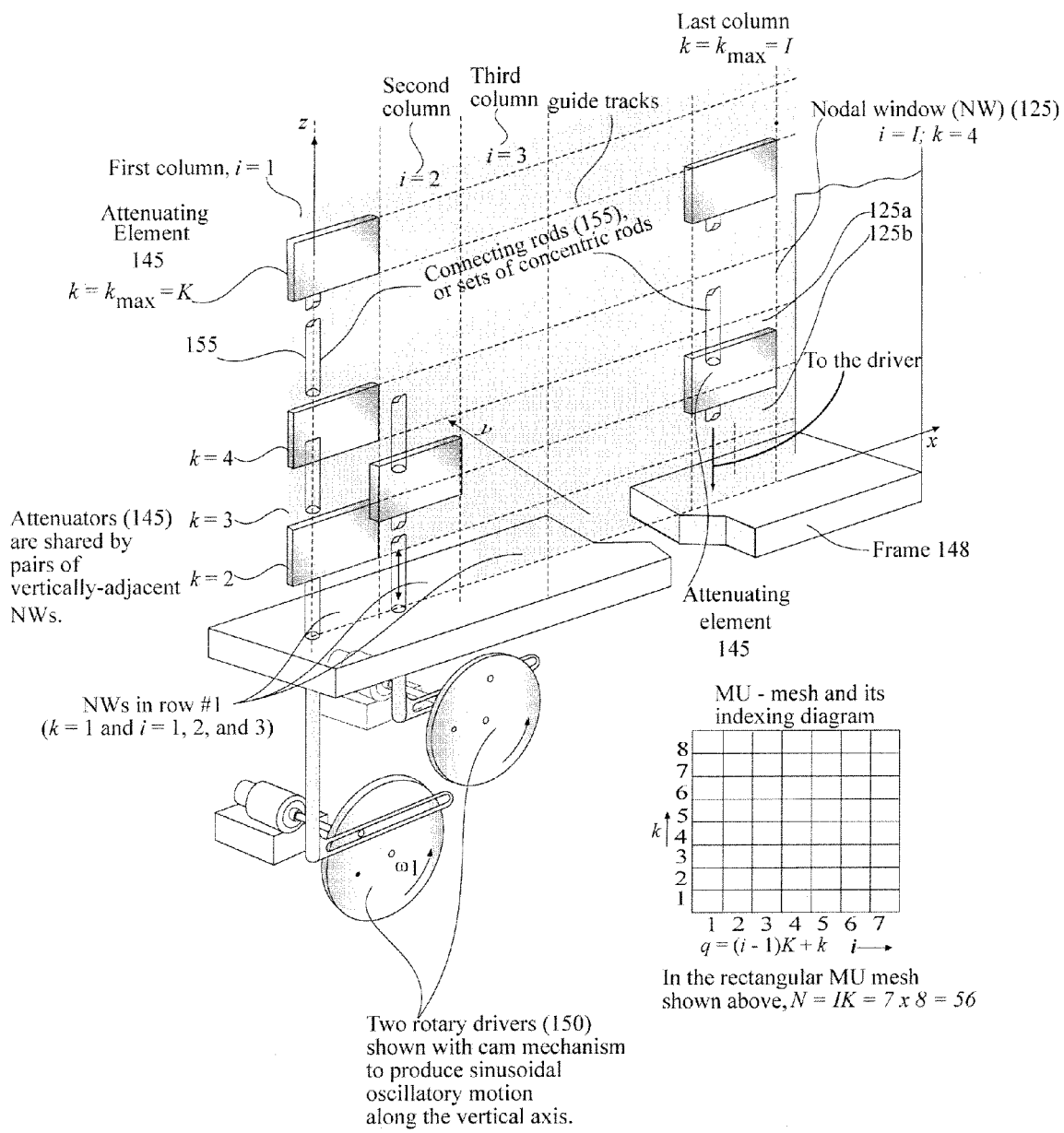
FIG. 4 depicts a rectangular modulating unit (Modulating unit) according to an embodiment of the invention.

In a simplified version of the rectangular modulating unit 120 shown in FIG. 4, each attenuating element 145, located in a column, may be attached to a common thin vertical rod 155, with spacing between adjacent elements in the column equal to or close to the vertical dimension of the window 125. A frontal view of the exemplary modulating unit column in FIG. 4 shows a series of connected elements alternated by vacant spaces, which make up a total of K passages in each column through which gamma rays may stream. The number K of passages may or may not be the same as the number N of NWs 125 in a column. This embodiment incorporates the sharing of one common attenuating element 145 by a pair (125a and 125b) of adjacent NWs in each column of the modulating unit, as shown in FIG. 4 when the attenuator 145 slides in an upward and downward motion.

The time-variant oscillation that modulating unit 120 imposes on the intensity of the gamma fluxes which pass through the modulating unit, is not uniform across the area of the modulating unit. Modulating unit 120 may be configured, in an embodiment, so that the time-variant oscillation varies in a two-dimensional space, across the plane (the cross-sectional area) of the modulating unit. FIG. 4 illustrates a view of the cross-sectional area of modulating unit 120 which may be designed to represent a matrix of window-like openings, referred to as NWs 125 and their associated attenuating elements 145. Each attenuating element or attenuator 145 exhibits a unique time-dependent oscillatory gamma attenuation upon the portion of the gamma ray stream moving through the particular NW 125 towards detector 115 (or alternately, toward the inspected object 105).

The exemplary modulator unit 120 shown in FIG. 4 is designed for periodic translatory oscillation (e.g., sinusoidal) of the gamma attenuating elements. In the coordinate system selected, x is the lateral direction across the face of the modulating unit, y is perpendicular to the plane of the modulating unit (in the mean direction of the gamma flux), and z is the vertical direction in the modulating unit plane. Attenuating elements 145 may be rectangular slabs of tungsten mounted on vertical rods that move in the vertical direction. The array of such attenuators is made up if K rows and I columns in the (x, z) plane. Each elementary areal space in the (x, z) plane is designated as a NW 125 and is identified by the subscripts i (along the x direction) and k (along the z direction) representing the row and column, respectfully, in which the NW resides. The term "nodal windows" may be represented by the symbol NW in the Figures. In each column, there may be an open space between adjacent attenuators, so that as the rods supporting the attenuators in each column oscillate up and down, each NW is alternately blocked and unblocked. Each depicted attenuator serves two vertically adjacent NWs in a column, causing the opening of one window to correspond to the closing of the adjacent window. All attenuators in the same column are connected to a common rod. A solenoid-driven sliding actuator may be used to substitute for the cam mechanism shown in FIG. 4. While electric power is convenient for the rotary drive, other power sources may also be used. The attenuators in each column can move along guide tracks, indicated by the vertical dashed lines. Alternately, upper and lower shaft bearings may be designed to serve as guides for shafts.

Figure 5:
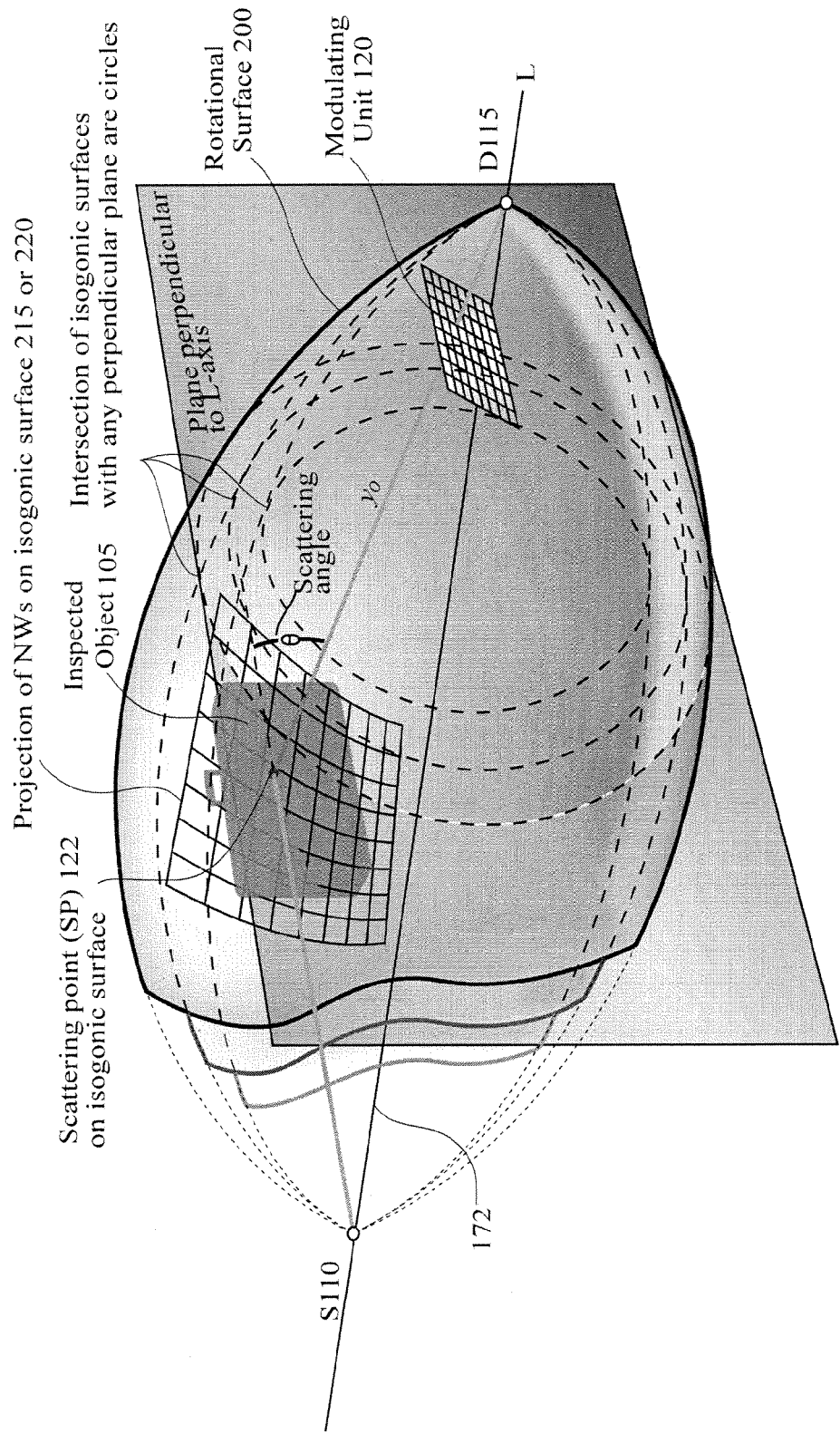
FIG. 5 is an illustration of the virtual projection of the modulation unit's nodal windows (NWs) upon spheroidal isogonic surfaces according to an embodiment of the invention.

The modulating unit 120 may be placed in the path of the gamma rays so that the cross-sectional area is perpendicular to the average direction $y_o$ of the fluxes transmitted from inspected object 105 and arriving at the detector 115 (or alternately, from the source and arriving at the inspected object). The design and arrangement of the NWs 125 and their attenuating elements 145 enables the imposition of a unique time-dependent oscillatory attenuation of the particular gamma flux segment that passes through each window. By employing multiple windows, with each attenuating element moving independently of other elements, modulating unit 120 uniquely encodes each segment (defined by the NW) of the gamma stream cross section incident on the modulating unit (or alternately, coming from the source 110 and incident on the inspected object 105). Each of the solid-angle segments of the gamma stream is associated with its particular NW 125, and defines a solid angle through which the particular gamma flux propagates. The solid angle is the angle that the NW subtends with the detector 115 (or alternately, the source 110 when the modulating unit is positioned between the source and the inspected object) as the apex of the subtended angle. As a result, for the detected gamma rays which are scattered from any volumetric element (voxel) within the inspected object 105, the voxel's center being the scattering point (SP) 122 as shown in FIG. 5, and the resulting local flux intensity can be characterized and identified by association of the NW's location with respect to the corresponding voxel within the inspected object 105. The term voxel, which is derived from volumetric pixel, pertains to elementary, small, but measurable finite-difference volumes. The term local flux refers to the gamma flux emanating from the point of scattering SP within the inspected object 105. More precisely, the term local flux refers to the averaged flux from within its associated voxel.

Each attenuating element or attenuator 145 exhibits a unique time-dependent oscillatory gamma attenuation; the functional time variance generated within each NW 125 of the modulating unit represents the encoding of passing gamma fluxes and is window-specific. The functional time variance may be accomplished by means of translatory or rotary movement of the attenuating element 145 relative to the individual NW's frame 147. The frame of the NWs can be either a hardware component, or a virtual frame that defines the NW's boundary, resulting in virtual NWs. The movement of the attenuating element causes a partial blocking of the NW, as shown in FIG. 4, and affects the magnitude of each solid-angle segment of the gamma ray stream as the gamma rays pass through the modulating unit 120. This translatory movement may be generated, for example, by attaching rotary drivers 150, as shown in FIG. 4, to the base frame 148 of the modulating unit 120 to vary the position of the attenuating elements 145. The rotary drivers 150 of the modulating unit 120 enables movement of attenuating elements 145, through the use of any known connection devices such as a hinge connection, linking device, or rotating shaft.

In the embodiment shown in FIG. 4, of the total number of columns I; only the first and second of these columns including their rotary drivers are shown attached to their cam mechanisms, which can be driven by an electric motor. The rotary drivers may be designed to produce a sinusoidal oscillatory motion along the vertical axis of the modulating unit 120. The rotational motion of the rotary drivers 150 is transferred to the oscillating attenuating elements 145 to vary the time function of their attenuation. Thus, this movement of the attenuating elements 145 affects the flux of passing radiation within each solid-angle segment leaving the modulating unit 120, traveling on its way to the detector 115. A computer, capable of executing data processing instructions, can be coupled with or integrated within system 100 to control and execute the analytical functions of the invention. Also, through the use of a computer or similar device (not shown) the motion of the attenuating elements 145 may be programmed to result in amplitude modulation (AM), phase modulation (PM), frequency modulation (FM), or a combination thereof.

The design of the modulating unit 120 can be configured or modified so that the invention can be utilized in a variety of modulating unit configurations. However, as discussed above, the physical attributes of the inspected object may be a factor for consideration in designing the modulating unit for a particular application. The system 100 can be designed (among other options) to include a rectangular modulator 120a (FIGS. 4 and 6) or a polar modulator 120b (FIGS. 7 and 8). In the rectangular embodiment, modulating unit 120 may be configured as a two-dimensional rectangular array of gamma attenuating elements. The attenuators 145 may be fabricated in a number of different ways, for example, as discrete elements, virtual portions of a number (1) of helical (twisted) strips, or as a single monolith sine-curve shaped attenuating block (not shown), that slides laterally across the NW's cross-sectional area. The rectangular modulating unit in FIG. 6 may be designed for rotary movement, causing periodic flux variation in rectangular gamma attenuating elements 145 which may utilize the same coordinate system as for the modulating unit shown as in FIG. 4, retaining the same notations for rows and indexing in the array of attenuators 145. Attenuating elements 145 may be rectangular slabs of tungsten mounted on vertical rotating rods. The illustration shows a modulating unit with 10 columns and 10 rows, corresponding to N=IK=10×10=100 NWs. Representative sets of attenuators 145 are shown only in columns #1 and #2. Attenuator elements are shown in various orientations on the driving shaft. The attenuation that each element offers is maximum when the face of the element is aligned with the face of the modulator unit frame (perpendicular to the direction of incoming gammas), e.g., in the NW corresponding to i=1, k=10 in the illustration. The attenuation is least when the attenuator element is perpendicular to the face of the Modulating unit (e.g., in the NW corresponding to i=1, k=6 in the illustration). The attenuation in each column can be made unique by the imposition of a different velocity of rotation of the supporting shafts. Uniqueness within the same column is achieved by the variation of the angular orientation of elements on each shaft (resulting in a phase lag). The thickness or height of particular attenuators can also be varied. The attenuation in a representative NW is characterized by the modulating function a(q, t). In it, $P_q$ is the phase lag of NW #q. The driving mechanism for each column shown employs electric motors, but other power sources may also be used.

Practical values for oscillatory modulation frequencies, selected by a user, may be within an order of magnitude of one per second. A suggested size for the modulating unit 120a may be between approximately several inches and a few feet in the lateral direction (perpendicular to the $y_o$ axis, representing the average direction of the gamma-propagation trajectories), with the thickness (in the direction of gamma-propagation) of the modulating unit's attenuator elements of the order of a fraction of an inch. The attenuator thicknesses may be influenced by the kind of gamma attenuating material selected. The modulator unit dimensions may be influenced by the scale of the overall size of the inspection system, especially considering the dimensions of the inspected object and the distance from the source and the detector.

In the simplified illustration of the rectangular modulating unit 120a shown in FIGS. 5 and 6, tungsten attenuating elements 145 are arranged in a matrix of I columns and K rows, forming a two-dimensional rectangular array of NWs 125, with the surface area of the window-array oriented perpendicular to the average direction $y_o$ of the oncoming gamma rays. The dimensions of the NWs may be the same or may vary throughout the entire modulating unit. Likewise, the thickness of the attenuating elements may be uniform, or vary from window to window.

Observing the dynamics of the system 100, when vertical driving rod 155 is in the lowest position, each NW 125 in the column is either clear or covered by an attenuating element. The invention may be designed so that when the rod is in the lowest position, all odd-numbered NWs may be blocked (providing maximum attenuation of their incident gammas), and all even-numbered NWs are clear (providing no attenuation of their incident gammas). When drive shaft 155 is at the highest position of its translatory oscillation, the situation is reversed so that all odd-numbered NWs are clear, while all even-numbered NWs are blocked and provide maximum attenuation to the incident gammas. As drive shaft 155 moves between the lowest and highest positions, all NWs undergo some degree of attenuation between the minimum and maximum attainable with their respective attenuating elements. The blocked and clear states of window transmission may vary in a sinusoidal (or other trigonometric function) manner as a consequence of the changing positions of attenuating elements, which is time-variant, as controlled by the sinusoidal (or other trigonometric function) oscillation of the vertical drive shaft 155.

In each column of modulating unit 120a shown in the example configuration of FIG. 4, a single vertical drive rod 155 supports several similar-sized gamma-attenuating slab-shaped attenuating elements 145. If each attenuating element slab 145 is shared by two adjacent NWs, the number of NWs for each column is N=2×5=10 NWs (for five such elements in a column). Each of the attenuating elements 145 may be designed with its unique thickness and height. All the attenuating elements 145 in a column may move at the same frequency since they are driven by the same drive shaft. However, the invention may also be configured so as to include separate (for example, concentric) drive shafts to control each attenuating element 145 individually so that the oscillation frequency of the elements may differ from each other. Also, each such individually-controlled attenuating elements 145, when moving independently of the others, could do so with its own time delay (phase lag) in motion.

Similar to the distinctions caused by varying the size (and/or even the material) of individual attenuating elements 145 within the columns of the rectangular modulating unit, operational distinctions in phase and frequency may also be incorporated to further generate unique variations of the gamma flux attenuation in each NW. The attenuating elements 145 can be oscillated up and down, individually or as a group, or by varying in time the position of individual attenuating elements within its associated NW. As depicted in FIG. 4, additional columns of attenuating elements are placed adjacent to the first column, making a total of I columns within the modulating unit. Each of these columns can be operated at a different oscillation frequency. For example, if I=40 such columns are included in the system, then the total number of uniquely oscillating absorbing elements would be 40×5=200. This embodiment provides twice that number (400) of uniquely-modulated NWs, since one attenuating element 145 serves two adjacent NWs 125, as discussed above and shown in FIGS. 4 and 6. Thus, the areal cross-section within the volume of the inspected object would include 400 pixels, corresponding to 400 voxels for each isogonic slice.

Of course, one having ordinary skill in the art will readily understand that the number of pixels (and the corresponding spatial resolution), may be designed to any convenient configuration, and the parameters of the modulating unit may also be of variable design. For instance, FIG. 6, which depicts an option for the operating rectangular modulating unit 120a, includes the vertical shaft 156 that turns the individual twisted rotating attenuating elements, instead of the vertically-moving elements as shown in FIG. 4.

FIGS. 7 and 8 illustrate an alternative embodiment depicting a polar modulating unit 120b. The polar modulating unit 120b may be designed using the same general concept as that of the rectangular modulating unit 120a, with a few notable exceptions. The polar modulating unit 120b includes a circular disk 152 fabricated of gamma attenuating material such as tungsten or lead. The disk 152 may be divided into a set of I concentric bands 153, all of which can have the same value of radial width $\Delta r^*$. Either the radial width or the thickness of the tungsten attenuator in each of the concentric bands 153 may be varied in order to generate a sinusoidal attenuation of the gamma flux. In other words, the amount of attenuation experienced by the portion of the gamma flux passing through a NW 125 of the disk 152 may be dependent on the designed variable radial width or the variable thickness (governing the attenuating power) of the attenuating material at the location of the NW 125. That NW 125 is a virtual entity, contained in a fixed position on the virtual stationary array of NWs superimposed on the rotating disk 125 of the modulating unit 120b. The NW area may be defined by the expression $[r^* \times \Delta \beta^* \times \Delta r^*]$. As indicated in FIG. 8, the symbol $\Delta \beta^*$ denotes the sector angle (of the order of degrees), the symbol $r^*$ denotes the radius, and the symbol $\Delta r^*$ denotes the width of the radial band. Reiterating the explanation provided with regard to the embodiment of the rectangular modulating unit 120a, variation in the attenuating power at a NW 125 may be the result of either a variation in thickness of material in the direction of propagation of gamma rays as they travel toward the detector/spectrometer 115, or a variation in radial width of the material inside the concentric bands 153.

In the polar modulating unit 120b, frequency modulation (FM) and phase modulation (PM) executed simultaneously provide a preferred method of effectively encoding each individual solid angle segment of the gamma flux passing through the modulating disk and arriving at the detector. This encoding is specific to particular locations on the virtual stationary circle, on which a NW 125 is defined by the radial band of width $\Delta r^*$, radius $r^*$, and polar angle $\beta$. These geometric pointers are associated with representative scattering points, i.e., the centers of scattering voxels, with their finite-difference area defined as conical projections of the virtual shadow of the NWs on the isogonics slices within the inspected object, as viewed from the detector.

FIG. 7, specifically, depicts how the time-varying attenuation may be generated in the invention when the thickness of the material is varied in the direction of propagation of the gamma rays in the polar modulating unit 120b. FIG. 8 illustrates an example of how the invention's modulating unit may be designed by varying the radial width of the attenuating material. The detector 115 views the inspected object by sensing scattered gamma rays impinging on the detector. For each pair of values $(r^*, \beta)$ the corresponding gamma-attenuating material performs a periodic attenuation according to the size and shape of the attenuating material and its motion. The radial band #i has i peaks of the sine curve, the next radial band has (i+1) peaks, etc. The number of peaks defines the modulation frequency for the band under consideration for any given speed of rotation of the disk. In general, the polar modulator shown in both FIGS. 7 and 8, can be designed to rotate with a constant, relatively slow angular velocity (of the order of 1 to 10 revolutions per second) about its center.

As an example, five concentric bands (with average radii $r_4^*$, $r_5^*$, $r_6^*$, $r_7^*$, and $r_8^*$) are shown in the polar modulator 120b in FIG. 7. There is a graduation of shading, from very light to very dark, going along the circumference. In this embodiment, the dark regions represent the positive peak areas of a sine-wave variation in thickness of the attenuator material—or maximum thickness—and the light areas represent negative peak areas, or minimum thickness. The attenuation of gamma rays passing through the disk is greatest at the location of the dark areas (where the material is thickest), and least at the light areas (where the material is thinnest). The band centered at a radius $r_7^*$ has seven very dark areas, representing seven complete sine-wave cycles. Each positive peak in that band is separated around the circle by an angular interval $\Delta \beta = 51.4$ degrees. The next outer band, $r_8^*$, has eight cycles, separated by an angular interval $\Delta \beta = 45$ degrees. As the disk 152 turns through one complete rotation of 360 degrees, each band may be out of phase with the next outer band by one complete sine-wave cycle. The sine-wave frequency is a bit higher for each successive outer band. For example, the band at $r_8^*$ experiences eight cycles in the same time period (one rotation of the disk) that it takes the next inner ring to experience seven cycles. The next two inner bands exhibit six and five cycles, respectively, with increasingly lower frequencies. This illustration can be expanded to incorporate any number of concentric bands. Further, the positions of bands having specific frequencies of oscillation, may be ordered in any sequence.

During a steady rotation of the disk 152, the traversed arc-length measured with respect to a stationary point next to the disk is proportional to time. Therefore, phase modulation PM is a characteristic that naturally occurs in this embodiment. For such a situation, the following may be implied: consider two adjacent NWs 125 in the same radial band of the polar modulating unit as shown in FIG. 7. If the attenuation in the left NW corresponds to a peak of the sine wave, then the right NW experiences a smaller, slightly delayed, off-peak attenuation. With clockwise rotation of the modulating unit 120b, the sine-wave peak moves to the right NW, leaving the left NW with a smaller off-peak attenuation. The difference in the attenuation between these two NWs is characterized by a time lag which is proportional to the phase angle difference $\Delta \beta$ between the left and the right NWs on the radial band. Related to the use of phase modulation, the sizes (thus, the boundaries) of the NWs in the polar modulating unit are also completely adjustable. Analogous to the options described with respect to the rectangular modulating unit employing rotating elements with helical attenuators 120a, the user of the polar modulator may also select values of the phase angle increment $\Delta \beta$ merely by entering a numerical parameter into the data processing computer program, without any adjustment of the physical apparatus.

For example, if the measurement system is set to resolve a difference in gamma intensities corresponding to $\Delta \beta$ equal to a 10 degree phase shift, then the polar modulator system would have K=360/10=36 phase delays (corresponding to 36 NWs along a column of a rectangular modulating unit 120a). The user can select the design of a system with I selected concentric bands. If I=20 is selected, there would be K=I=36× 20=720 pixels of information per virtual slice of the inspected object, which pixels are available to reconstruct the image of one isogonics slice within the inspected object. Use of finer phase resolution (e.g., by choosing $\Delta \beta$ less than 10 degrees) together with additional radial bands in the modulator disk 152 can provide for several thousand pixels in a reconstructed image of an isogonic slice. Using 720 pixels per slice, if 20 slices are considered (i.e., 20 energy values of scattered gammas), the resulting resolution would be represented by 720× 20=14,400 voxels inside inspected object 105.

While in FIG. 7, the thickness of the attenuator in the direction of gamma-propagation directly controls the NW-associated attenuation, that attenuation is controlled in FIG. 8 by varying the radial width of the band so that the gamma-attenuating area of the band at any point along its circumference varies in a sinusoidal manner, as depicted by the shaded area specifying the attenuator material exposed to gamma rays in a band's sector.

The design in FIG. 8, being is analogous to the design of FIG. 7 in regard to the periodic sine variation of attenuation, enables: (a) amplitude modulation (AM) as a result of the changing thickness of the attenuator material along the circumference of the disk; (b) frequency modulation (FM), utilizing the radial variation of the number of sine wave cycles; and (c) phase modulation (PM), having intrinsic phase delays among adjacent virtual NWs on each particular radial band, with a wide range of practical options for selection of the phase angle Δβ (i.e., time delay) between adjacent NWs.

In both polar modulating unit designs, the use of band-related FM supports the determination of the sub-total of gamma fluxes—i.e., all fluxes passing through any particular annular band—which is a component of the total flux passing through the entire cross-section of the modulating unit disk, i.e., through all its annular bands.

Regardless of the configuration, the modulating unit 120 constitutes a two-dimensional matrix of periodic, time-varying gamma attenuators, which modulate the gamma fluxes passing through the attenuator-associated NW.

Further, in an alternate embodiment of the invention, the modulating unit may be configured in a three-dimensional geometry, wherein the modulated gammas pass through more than one layer of NWs and their associated attenuators to serially-encode the individual streams of radiation.

The Integrated Modulator

As an alternative embodiment, instead of utilizing a separate modulator unit as described in the preceding discussions, the invention may be configured so that a modulator is incorporated as an integral part of either the detector or the radioactive source.

To integrate the modulation unit within the detector system 115, the system 100 may be configured by adapting the detector/spectrometer into a mosaic, with individual read-out from each element of the mosaic [is possible]. Such a configuration would allow the signals, generated by the incoming gamma rays incident on each mosaic detector element to be segregated and processed separately. Electronically controlled modulation of the bias voltage (in the case of a semiconductor detector) or a varying mosaic light filter (in the case of a scintillator and photo-multiplier tube detector) may impose the modulating function a(q, t), as described below, on the incoming signals. This signal perturbation would be equivalent to the operation of the external modulating units described earlier.

Alternatively, the modulation unit may be integrated with the radioactive source system according to the following manner. A customized stationary attenuating slab may be precisely shaped to produce a varying attenuation (along its length) of gammas traveling in a direction approximately perpendicular to the surface of the slab. As the source is raised from its storage position to irradiate the inspected object 105, the source would travel past the shaped attenuating slab. Thus, the source's two-stroke motion in and out of the shield cask would result in a designed modulation of the passing gamma flux according to the slab design, generating a transient (time-dependent) attenuation of the source gammas. This will result in a modulation of these gamma rays analogous to the a(q, t) modulation function impressed by the attenuator elements in the modulating unit.

Radiation Detector Requirements

Referring back to FIG. 1, the radiation detector 115 may be a gamma spectrometer, which is a device that detects individual gamma photons that impinge upon the detector 115 and provides an output signal that is proportional to the energy of the detected gamma photons. The size of the detector may be configured to be small in comparison to the size of the inspected object 105 and to the distance between the detector 115 and the inspected object 105. In the analysis performed by the invention, the detector may be approximated as a point in space, to simplify the geometrical assumptions in the analysis.

During operation of the system 100, optimal positioning of the source and detector is partially dependent on the size and shape of the inspected object 105, with the cone of radiation emerging from the source directed toward the inspected object 105, encompassing the region to be inspected.

Compton Scattering of Gamma Rays

The operation of the inspection system 100 also takes advantage of the relationship between the energy of scattered gamma rays and the angle of scattering, expressed as the Compton Law, and explained by H. Semat, *Introduction to Atomic Physics*, Rinehart & Company, Inc. Publishers, New York, 1947, pp. 144-145 and J. R. Lamarsh, *Introduction to Nuclear Engineering*, 2d ed., Addison-Wesley Publishing Company, 1982, pp. 81-88. Both of these publications are hereby incorporated by reference.

As shown in FIG. 2, the Compton Effect refers to the process in which a gamma photon or X-ray of energy $E_o$, incident on a target, interacts with the atomic electrons in the target material. This process results in a scattered photon being emitted at an angle "theta" from the direction of the incident photon with a reduced energy E', and a recoil electron emitted at an angle θ*.

The relationship between the energy of the scattered photon and its angle of emission has been established and reviewed by a number of authors. Lamarsh notes that the energy-angle relationship for Compton scattering is given by the expression in Equation (1) below.

E' is the energy of the scattered photon, $$E'=E_o E_e/[E_o(1-\cos\theta)+E_e]$$  Eq. (1)

E' is the energy of the scattered photon, $E_o$ is the energy of the incident photon, θ is the angle of deviation of the scattered photon from the direction of the incident photon, and $E_e = m_e c^2 = 0.511$ MeV is the rest-mass energy of the recoil electron.

For a mono-energetic incident gamma flux and defined source location, the Compton relationship allows one to determine the angle (i.e., the direction) from which the scattered gammas originated, based on the measurement of the energy of detected scattered gammas. A gamma ray detector/spectrometer 115, such as described above, may be used to separate out the energies of the gamma counts registered by the detector 115. Employing such instruments over a broad range of energies enables system 100 to simultaneously measure the energies and the intensities (count rates) of all detected gamma photons, which are predominantly scattered within the inspected object 105. This measured energy spectrum of scattered gamma photons and their associated count rates (proportional to the magnitude of the flux of scattered gammas) are geometrically related to the corresponding directions and locations in the examined space.

Formation of Isogonic Surfaces

A triangle, as shown in FIGS. 3A-C, may be formed by three points in a plane including the location of the radiation source at point S; the location of the scattering point at point SP somewhere within the inspected object; and the location of the detector at point D. The distance between the point S and the point D is L* (the base of the triangle), shown as segment 172.

The Compton energy-angle relationship can be illustrated by the geometrical attributes of such a triangle. For example, if a half-circle is drawn above a triangle's base, with the circle's center in the mid-point of the base, wherever the upper tip of the triangle is located on that arc, the subtended angle from that tip (towards the triangle's base) will always be 90 degrees (as shown by Case II of FIG. 3b). This axiom can be extended to the more general case: if the system deals with a smaller (flatter) arc of the circle rather than a half-circle— meaning that the center of a new circle would be below the middle of the base of the triangle—all the new subtended angles will again be equal among themselves, but smaller than 90 degrees (Case I of FIG. 3a). Each tip-angle is a function of the length of the new arc's radius; that depends on how far the center of the new arc is below the mid-point of the triangle's base. Conversely, if the center of a new arc is above the triangle's base, such an arc would not be flatter, but more curved (Case III of FIG. 3c). The arc's center location and its radius are known functions of the distance L* and the scattering angle $\theta$, as derived and initially published by N. Kondic, *Density Field Determination by an External Stationary Radiation Source Using a Kernel Technique*, Symposium on Poly-phase Flow Measurement, ASME Winter Annual Meeting, San Francisco, Calif., December 1978. The subject matter of this publication is also hereby incorporated by reference.

The above observations may be applied to two-dimensional space. However, it is within the scope of the invention to extend and apply these observations to three-dimensional space. Any of the arcs considered here can be rotated about the triangle's base, which is denoted as the line that joins the source and detector points referred to as the S-D segment 172 in FIG. 3. Such a rotation creates a surface, which, in the case of relatively flat arcs, may resemble a blimp 200, as shown in FIGS. 3a and 5. In this manner, the constant scattering angle is actually associated with all points on the arc-generated surface of rotation, where each such surface's shape corresponds to a particular value of the scattering angle θ. These surfaces are referred to as isogonic surfaces, since each surface of rotation is the locus of scattering points for gamma photons emanating at the same scattering angle. The portion of the isogonic surface within the inspected object is referred to as the isogonic slice (FIGS. 5 and 9); it forms the loci of scattering points producing gamma fluxes within the cone of view of the detector (the $y_o$ axis is in the mean direction of the inspected object's depth measurement). When the scattering angle θ changes, the shape of the rotating isogonic surface will change (it will become more flat or more curved), and according to Eq. 1, the energy of the scattered gamma rays will also change. FIGS. 3A-3C illustrates the dependence of the isogonic surface's shape on the scattering angle θ. From a flat blimp shape 200, corresponding to smaller scattering angles, that shape becomes a sphere when theta reaches 90 degrees. When the scattering angle increases beyond 90 degrees, the contour swells into a double spheroidal shape. FIGS. 3A-C illustrates the geometric aspect of Compton's Law that lends itself for application by a device which may be employed in the invention. In summary, Compton's Law may be applied to the invention by utilizing any of the three types of isogonic surfaces: Case I—Oblong rotary surface with pointed poles (the SD segment is located above the circle's center) (FIG. 3a); Case II—Sphere (the SD segment passes through the center of the circle) (FIG. 3b); and Case III— double spheroidal rotary surface with indented poles (the SD segment is below the circle's center) (FIG. 3C).

The application of Compton's Law to the inspection measurements performed by the invention allows the system 100 to yield information on the distance along the path of gamma rays emanating from the source, with scattering points forming a defined curved isogonic surface (FIG. 5) of a known shape that intersects with the distance axis $y_o$ along the gammas' trajectory. The novel modulators (described above) are used in a determination of the distribution of single-scattered gamma fluxes across the isogonic surface, i.e., along the two remaining axes of the inspected three-dimensional density field, these being x and z for rectangular modulators, and r* and z for polar modulators.

The modulating unit 120 may consist of a two-dimensional matrix of time-varying gamma attenuators 145, which modulate the fluxes passing through them. The modulating unit 120 is placed in the path of the gamma rays, either between the source and the inspected object or alternately, between the inspected object and the detector. Considering the latter position, each particular segment of "local" scattered gamma flux of constant intensity (associated with a particular voxel) incident upon a particular NW of the modulating unit can be encoded in time, by varying its intensity in time while passing through a NW. The modulation, i.e., the encoding imposed on flux segments, is unique for all flux segments coming out of any particular voxel (volumetric pixel) located along a given axis $y_q$ within the inspected object. Such flux segments pass through the $q^{th}$ NW which is associated with a particular axis $y_q$. The modulation may be decoded from the signal output of the detector 115, employing a multi-stage data-processing system to yield the flux of scattered gamma rays as a function of three coordinates of the scattering point (or voxel): two directions ($x_q$ and $z_q$) across the modulating unit 120, the third being the depth $y_q$ within the inspected object 105. The third coordinate may be obtained from the known location of isogonic surfaces, derived from the gamma energy-angle relationship cited in describing the Compton scattering process, as discussed above.

In accord with the cited Compton Law, for a particular source energy $E_0$, anywhere in the surrounding space where the scattering angle is constant, the Compton scattering phenomenon: (a) results in the same measurable energy of scattered gamma rays, and (b) has to occur on a particular isogonic surface, noting that the location and shape of such surfaces are independent of the presence, shape, material, and size of any inspected object and its internals.

Therefore, from these geometrical attributes, the invention demonstrates that, when a mono-energetic radiation source emitting gamma rays into the surrounding space is placed at one fixed end-point of the isogonic arc and the detector is placed at the other fixed end-point of the same arc, an isogonic surface (that includes all the arcs forming it) can be completely defined for a given energy of the scattered gammas. That surface of rotation comprises all the loci within the surrounding space, which send constant-energy single-scattered gammas in the directions specified by the scattering angle θ, including the direction of the detector.

For any scattering angle and the corresponding shape of the associated isogonic surface, within small finite energy intervals in which finite numbers of scattering events occur, gamma photons can be detected. Each isogonic surface may be associated with a certain finite thickness, so that, in practical application, the invention deals with thin volumetric entities built upon the isogonic surfaces. These entities are termed isogonic shells. Since the source and detector are external to the inspected object, the widely extended isogonic shells virtually intersect with the inspected object. The portion of the isogonic shells that extend beyond the boundaries of the inspected object (as illustrated in FIG. 5) need not be considered. The useful portion of the isogonic shells, which are confined by the object's boundaries are termed isogonic slices. Since the isogonic slices are geometric notions rather than physical entities, they are referred to as virtual slices. The virtual slices are thin three-dimensional portions of the fully-extended three-dimensional virtual isogonic shells. The intersections of the inspected object and isogonic shells can result in various geometrical configurations of virtual slices, some of them illustrated in FIGS. 5 and 9.

Figure 9:
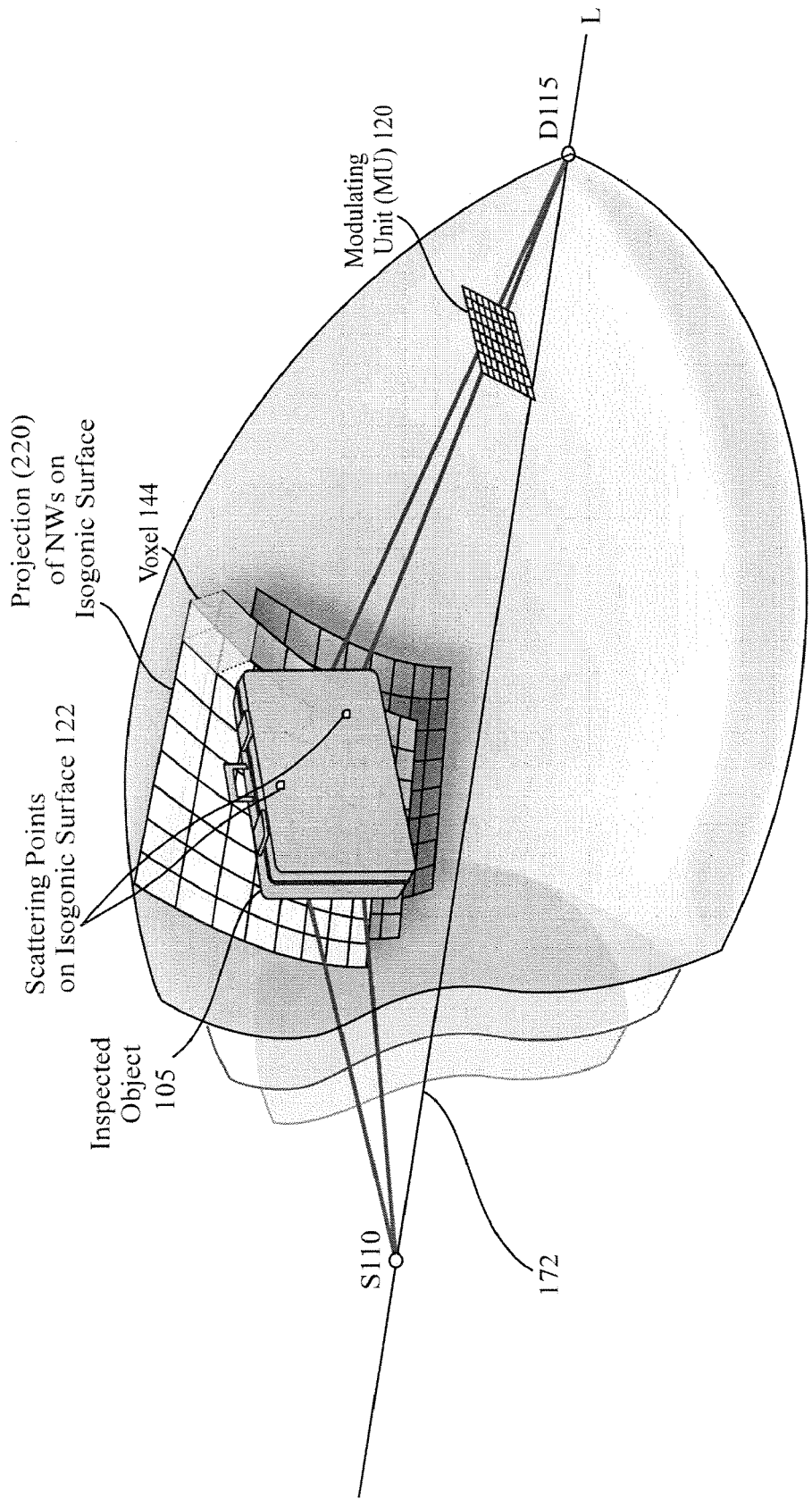
FIG. 9 shows a virtual projection (viewed from the detector), of a rectangular array of NWs on isogonic shells and surfaces within and around a proximate region of the inspected object, forming virtual voxels from which scattered gammas emanate and travel toward the detector.

The pyramidal projection 220 of the rectangular modulating unit's NWs (FIG. 9) may intersect all the isogonic surfaces and their associated thin shells, thus projecting curved quasi-rectangular patterns upon the slices within the inspected object 105. As can be seen in FIGS. 5 and 9, the contour of these patterns follows the shape of the curved isogonic slices introduced earlier. Since each such slice is a portion of its corresponding isogonic shell (which is the loci of all the scattering events resulting in gamma rays of the same energy emerging from that shell and registered at the detector), the total number of observed slices is the same as the number of isogonic surfaces and shells. That number, equal to $J=j_{max}$, is also equal to the number of energies ($E_1'$, $E_2'$, ... $E_j'$, ... $E_J'$) of single-scattered gamma rays considered in the analysis as well as of the number of energy bins utilized in the multi-channel pulse height analyzer.

FIGS. 5 and 9 depict an illustration of spatial scattering geometry upon spheroidal isogonic surfaces with scattering angles ≦90 degrees. As indicated in FIG. 1 and stated earlier, the gamma rays that are emitted by the radioactive source, prior to scattering interactions within the inspected object, retain their original energy and direction (radiating isotropically from the point source). However, the scattered gamma rays, which are generated when the primary gammas interact with atoms, are predominately generated within the space inside the inspected object, which is filled with virtual isogonic slices, defined earlier to be of small, but finite thickness. An example of the orientation and size of the virtual slices is depicted in FIG. 9. This sub-division of the inspected object's volume into a finite number of virtual slices aids in the data acquisition and processing, and is related to the desired spatial resolution and optimal placement of the source, detector, and the inspected object.

Referring to FIG. 9, the grid 215 (with NNWs corresponding to N voxels 144 per slice), represents the virtual projection upon the surface of isogonic shell #1, of all NNWs in the modulating unit 120. Gamma rays from the radioactive source scatter in any of the J isogonic shells; for simplicity, only shells 165a, 165b, and 165c (in the vicinity of the inspected object) are shown in FIG. 10A. A portion of the scattered gamma rays passes through the modulating unit as they travel toward the detector (D) 115, where gamma counts caused by detection of gamma rays arriving from particular isogonic shells are stored in separate bins of the MCA 135. The energy of the detected gamma rays (which are registered by the detector/spectrometer and MCA) provides a direct link to the isogonic slice (#1, #2, ... #i, ..., or #j) from which the gammas are scattered.

In summary, single-scattered gamma rays which reach the detector are generated within a selected number J of virtual shells. The portion of each virtual shell 165 that is within the inspected object is called a virtual slice, and represents a thin volumetric section of the inspected object. Each shell 165 is virtually illuminated by an expanded, pyramidal (for the case of the rectangular modulator—or conical, for the case of the polar modulator) projection 220 of the modulating unit. This virtual projection 220 occurs from the pyramid's (or cone's) apex at the detector, looking towards the inspected object. Since the $y_0$-axis passes through that apex (which is the center of the detector) and the center of the modulating unit's cross-sectional area, the $y_0$-axis also passes through the centers of the modulator's projection on all virtual slices, thus specifying their location, as indicated in FIG. 9. Since the energy $E_j'$ of each scattered gamma ray geometrically defines a specific j-th isogonic slice, the value of $y_{0j}$ (which is the inspected object depth coordinate) at the intersection of the y-axis and the j-th isogonic virtual slice becomes known, and can be denoted by $y_0(E_j')=y_{0j}$. Accordingly, based on a measurement of the energy of single-scattered gammas, the system can determine one of the spatial coordinates $y_{0j}$ of any j-th slice, on which the scattering points are located within the inspected object. Regarding the scattered gammas, the output signal of the gamma detector/spectrometer D is continually inputted into the MCA 135, which sorts the various scattered gamma counts according to their voltage pulse height (energy). Each of the J energy bins of the MCA 135 stores and displays the gamma counts during any given measurement period. These counts correspond to the detected scattered gamma photons having energy values within the bin's narrow energy band $\Delta E_j'$, with energy $E_j'$ in the center of the band. The number of counts stored in the $j^{th}$ bin represents sub-totals of the gamma fluxes and encompasses all scattered gamma photons from within a particular entire isogonic shell. Therefore, the counts consist of gamma fluxes from all individual voxels within the isogonic slice 165 (within the inspected object) and the portion of the isogonic shell 165 outside the object. All of these gammas have the same energy, $E_j'$. The total set of gamma fluxes scattered from the observed portion of the inspected object is the sum of sub-total modulated fluxes, encompassing all gammas scattered from all J isogonic slices (summed up from all J bins of the MCA 135), and which pass through the modulating unit 120. Another aspect of the invention is to identify and separate gamma fluxes which originate from scattering events occurring in a large number of volumetric elements included in an isogonic slice. These elements are individual voxels 144 having a known location and shape. The separation of fluxes enables the invention to calculate the magnitude of local fluxes coming from the individual voxels 144. At the same time, the invention is also capable of eliminating from consideration those single-scattered fluxes arriving at the detector from portions of isogonic shells 165 external to the inspected object. Those fluxes do not bear information on the density field inside the inspected object.

Operational Diagram of the Inspection System

Figure 10B:
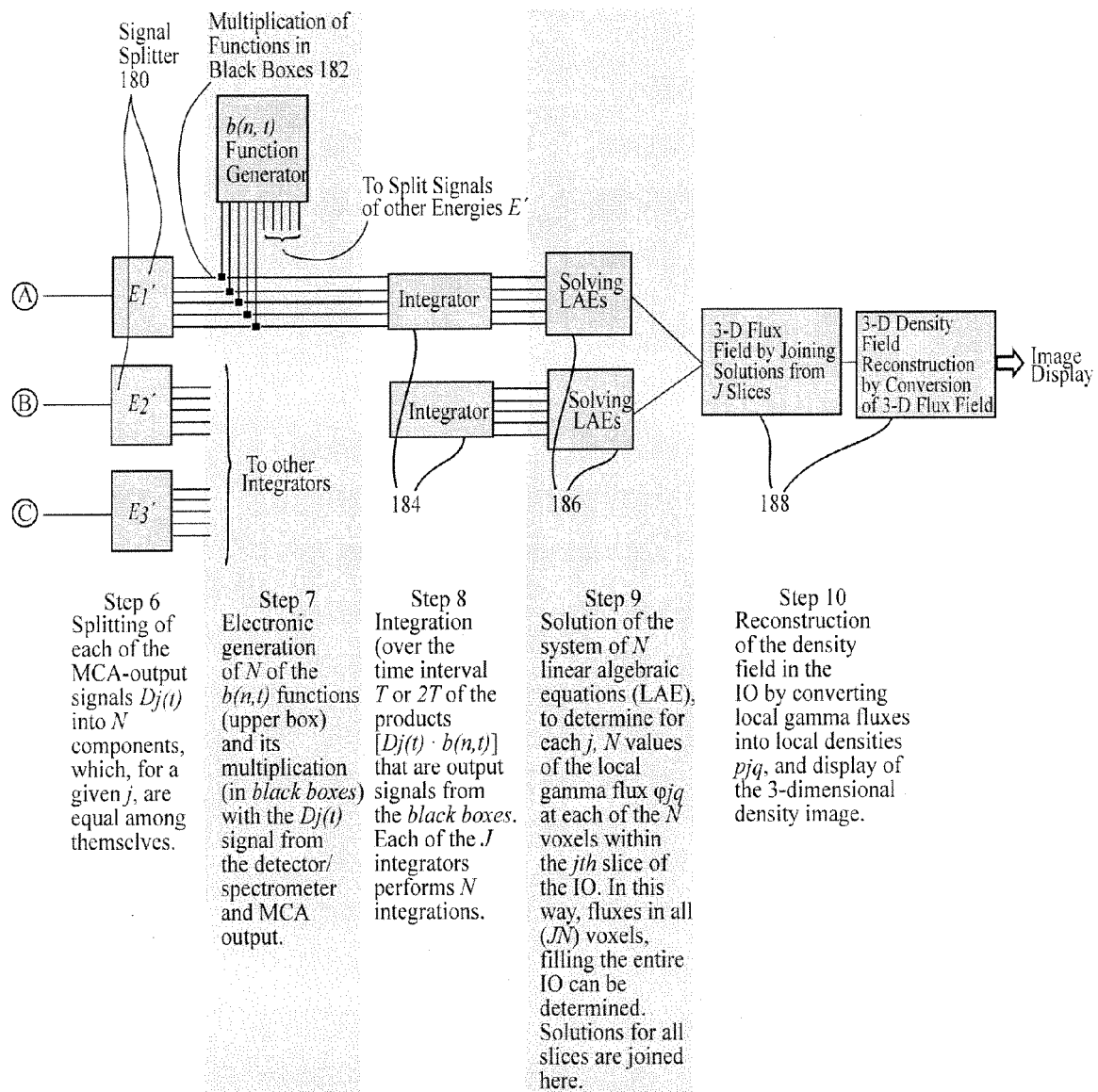

FIGS. 10A-10B provides a diagram of the process of generating three-dimensional images according to an embodiment of the invention. In Step 1, an inspected object is irradiated by gamma rays emanating from an isotopic source 130. The isotopic source 130 may be, for example, a mono-energetic gamma source having a constant stream of gammas with energy $E_0$. As shown in FIGS. 1-2, when the gamma rays interact with atoms inside the inspected object 105, scattered gammas 113 having energy E' are emitted from voxels within the inspected object and a measurable fraction of the scattered gammas 113 travel in the direction of the modulator 120 and the detector 115, in this particular embodiment.

In Step 2, the single-scattered gamma flux $\phi_{jq}$ having energy $E_j'$, which emanates from the virtual isogonic slice #j in the inspected object, passes through the $q^{th}$ NW of the modulating unit, and detected by the detector, is determined by the invention. By applying the Compton Law for an incident gamma energy $E_0$, the scattered gamma ray energy $E'(\theta_j)$ can be determined using Eq. 1. The invention may be configured so that one of the objectives of this embodiment of the invention is to concentrate on only the count rates from gammas scattered within that portion of the shell 165 which is inside the inspected object, onto which portion the modulating unit's field of view is projected, as depicted in FIGS. 5 and 9. As previously discussed, that portion of the isogonic shell 165 is referred to as a virtual isogonic slice. Since only gammas scattered from within these virtual slices carry the signature of flux- and density-distribution within the inspected object, only these gammas are of interest to this embodiment of the invention and therefore are encoded by the modulating unit 120.

The invention determines the values of N local densities (one per NW) within each of J intersections of the virtual projection of the modulator (as viewed from the detector) with J particular isogonic shells 165, whereby these intersections define the virtual isogonic slices of interest. Before calculating the local densities, the invention, in Steps 2-5, identifies the location matrix and intensities of N unmodified single-scattered gamma fluxes. The location matrix is the same for material densities and local gamma fluxes. The term "local" refers to the location at the point of scattering and its associated voxel within the inspected object. The location matrix of the volumetric pixels (voxels) within the inspected object may be defined by the location and shape of the isogonic slices, as well as orientation and design of the modulating unit and detector. These single-scattered gamma fluxes are the time-independent gamma fluxes generated by single Compton scattering inside the inspected object and incident upon the modulating unit on their path towards the detector. After passing through the modulating unit, the magnitude of these fluxes becomes somewhat reduced from that of the incident gammas, and the fluxes become time-dependent upon passage through the oscillating attenuator elements of the modulating unit.

The scattering events and attenuation phenomena within the inspected object are carefully considered using the appropriate equations that characterize them. These events and phenomena enable an unambiguous numerical characterization of the density distribution within the irradiated inspected object.

The scattering formula, shown below as Eq. 2, describes the relationships of variables associated with gamma scattering phenomena, and can be used to calculate the scattered gamma flux. The formula is applicable when no modulation takes place in the paths of the gammas.

$$\varphi_{jq} = (Q^*)(C^*)[(\Delta V_P/R^{*2})_{jq}(\rho_{jq}K^*_{jq})(1/H^*_{jq})^2(P_oP')_{jq}]P''_{jq} \quad \text{Eq. 2}$$
$$= (Q^*)(K^*_{jq})(\rho P_o P')_{jq}(P''_{jq})(G^*_{jq})$$

In the above equation:

$\phi_{jq}$=the gamma flux, expressed as the number of gamma photons per second passing through one cm of area A* perpendicular to the trajectory of the gammas, at a distance H*, which is the distance between the scattering point (SP) and the center of the area through which gammas pass, anywhere along the distance axis h. The h axis may coincide with the y axis.

$R_{jq}^*$=the distance from the source's center to the SP, which is defined—in the manner of other indexed parameters—by the pair of location subscripts jq, where j specifies the scattering slice and its corresponding gamma energy, and q specifies the location of a NW within the modulating unit.

Q*=the source strength (in Curies), related to the number of gamma photons emitted per second.

C*=$(3.7 \cdot 10^{10})/(4\pi)$—a constant, that transforms the unit of Curies into the number of disintegrations per second over the unit solid angle, i.e., the number of gammas emanating from the source per steradian per second.

$\Delta V_P$=the volume of the scattering voxel (volumetric pixel), a small, but finite size volume, that generates a measurable stream of gammas, considered as the average stream value exiting that voxel, and associated with its center-point—which is the SP.

$\rho$=the electron density (proportional to mass-density of material) in the voxel.

K*=the local Klein-Nishina scattering probability (a tabulated physical property). The probability of single-scattering of gamma photons in the Compton process was calculated by Klein and Nishina on the basis of relativistic quantum mechanics, and is discussed by Irving Kaplan in *Nuclear Physics*, Addison Wesley Publ. Co., $2^{nd}$ Ed., March 1964, which is incorporated by reference.

G*=a composite geometrical parameter, grouping known constants, distances, areas, and volume, appearing in the above equation, corresponding to scattering from SP.

$P_o$=probability that the incident gamma photons from the source will not interact with the attenuating substance of the inspected object during their transit inside the inspected object, prior to scattering.

P'=probability that single-scattered gammas emanating from the inspected object will not interact with the attenuating substance of the inspected object during their transit inside the inspected object, after scattering.

P'''=probability of the non-attenuation of gamma photons resulting from their transit through both walls of the inspected object (upon entering and exiting the object).

The following two equations and the subsequent text define the non-attenuation probabilities $P_o$, P' and P''' appearing in Eq. 3. The abbreviation exp stands for the exponential function (where exp n=$e^n$).

$$(P_o)_{jq} = \exp[-k_o(E_o)\rho(r)dr] \quad \text{Eq. 3a}$$

$$(P')_{jq} = \exp[-k'(E_j')\rho(h)dh] \quad \text{Eq. 3b}$$

The invention requires integrations from the $SP_{jq}$ to the boundaries of the inspected object, defined as limits of the above integrals, along the r- and h-axis, respectively.

The variables r and h are spatial coordinate axes in the direction of gamma propagation, associated with distances R* and H*, respectively.

$k_o(E)$ denotes gamma energy-dependent specific flux attenuation coefficients for source gammas (of energy $E_o$), expressed as reaction area per electron.

k'(E') is the gamma flux attenuation coefficient for scattered gammas (E'=$E_j'$); here, the subscript; (used with P' and E') refers to a specific value of the energy $E_j'$ of scattered gammas. The term k' is expressed in the same units as k.

When the integral(s) in Eq. 3 are replaced by the product of a constant material density and the known path length of gammas through that material, $P_o$ and $P_j'$ become the directly-calculable non-attenuation probabilities for gammas transmitted through such materials, and is denoted by P'''. Thus, the term P''' can pertain to the boundary of the inspected object, a shielding structure, or an element within the modulating unit that is designed to partially block the transmitted gammas.

Eq. 2 can be re-grouped to define the term X in Eq. 4 below, as a property of the interrogated density field within the inspected object. This property expresses the interrelationship between the field of local gamma fluxes and the field of material densities, needed for carrying out the subsequent density field reconstruction task.

$$\kappa_{jq} = (\rho P_o P')_{jq} = \phi_{jq}/[(Q^*K_{jq}^*)(G^*PO)_{jq}] \qquad \text{Eq. 4}$$

In addition to the local (point) density, density integrals appearing in Eq. 3 are included in the P-terms of the above group; in a numerical analysis, each such integral can be expressed by an equivalent sum of local densities along a straight line, which is the integration axis.

In summary, the scattering equation, Eq. 2, describes the flux of single-scattered gammas streaming throughout a region having an unknown distribution of mass density, traveling along the h axis, through a unit area at a distance H* from the scattering point. The equation includes known or directly-measurable geometric and physical parameters, such as dimensions and physical properties of the media through which the gammas pass within the inspected volume.

In Step 3, the modulating unit 120 encodes the gamma fluxes by causing a unique periodic oscillation to be imposed on the fluxes within each NW of the unit. A steady flux of mono-energetic gammas emanates from the source S, and streams along a group of diverging straight lines which intersect with the virtual slices within the inspected object, as depicted in FIGS. 1, 5 and 9. Numerous gammas will scatter within the inspected object, as well as on portions of the isogonic shells 165 outside the inspected object. These latter extraneous gammas contribute to steady or random background noise signals registered by the detector. In order to eliminate or mitigate their effect, shielding may be used around the source and the detector to block extraneous multiple-scattered gammas. Further, analysis or data processing may be employed to eliminate or calculate the undesired scattered gamma fluxes, as well as the fluxes due to background noise, both categories of which do not originate from directly within the inspected object, and accordingly, cannot be associated with any reconstruction of the inspected object's internal density distribution. Additionally, single-scattered fluxes originating from within the inspected object may be calculated and their points of origin identified; the locations of these points cover all virtual slices, and thereby include all voxels within the volume of the inspected object, which means that the distribution of scattered gamma fluxes and corresponding mass densities within the entire volume of the inspected object can be mapped.

The known gamma flux from the source S irradiates all the virtual isogonic slices within the inspected object. A substantial fraction of these source gammas generates the scattered gamma fluxes, according to Compton's law, described by Eq. 1. The scattering equation, Eq. 2, gives information on the portion of un-modulated scattered gammas that reaches a specific location, e.g., the detector 115. Two observations should be noted:

- All of the detected single-scattered gammas coming from each of the virtual slices stacked along their trajectory leave the scattering voxels 144 and stream toward the detector. They are encoded as they pass through the modulator, similar to the situation depicted in FIGS. 5 and 9.
- The sub-division of the modulating unit area into NNWs-oriented to intercept gammas streaming toward the detector, and the window's virtual projection on the isogonic slices within the inspected object translates into a subdivision of the thin volume of each virtual isogonic slice into N voxels 144, the size of which determines the resolution of the reconstructed density image. FIGS. 5 and 9 illustrate how the modulating unit's pattern of NNWs translates into N voxels on each of J virtual slices.

Since only gammas scattered from within virtual slices carry the signature of flux- and density-distribution within the inspected object, only these are of interest to the invention in this embodiment. The field of view defining the projected pyramid (for the rectangular modulating unit), incorporates the entire matrix of NNWs (NW). As explained earlier and shown in FIGS. 4 and 6 through 8, a small oscillating attenuator element in each of these windows (or one element shared by two adjacent windows) encodes the gamma flux $\phi_{jq}$ passing through the window, enabling a unique identification of each angular segment of the gamma flux. This temporal encoding modulation differs from window to window. Such an operating arrangement, coupled with the Compton scattering law, provides the basis for the non-invasive determination of density distribution in an object. The Compton scattering law provides information on the scattering angle of single-scattered gammas, which is associated with a particular isogonic slice within the inspected object. That isogonic slice is, in turn, associated with the distance (y or h) from the detector traveled by single-scattered gammas. Additionally, the encoding by the modulating unit provides information on the location of the NW's projections on the virtual slices inside the inspected object 105. Thus, the role of the modulating unit is to label the gamma flux that passes through each NW of the modulating unit by a window-specific periodic attenuation of the gamma flux. The un-modulated single- and multiple-scattered fluxes, propagating externally to the virtual projection of the modulator or the inspected object (as viewed from the detector), as well as any other detected constant or randomly fluctuating background radiation, are eliminated by the integration that takes place in Step 8 of FIG. 10B.

In any particular NW of the modulating unit, the attenuation function imposed on the gammas by a modulating attenuator element can be described by the periodic function a(q, t), with q denoting the location of the element (the NW's attenuator) within the modulating unit, and t being real time.

For any energy $E_j'$ of scattered gammas, the single-scattered gamma flux incident upon NW #q, constant in time, as a specific expression of Eq. 2, is denoted by $\phi_{jq}$. Along its propagation direction, the periodic transient flux exiting the same NW is equal to the product of the steady incident flux and the relative transmission area of the NW, where the relative transmission is a function of time denoted by a(q, t), and is expressed by Eq. 5 below. The term "relative" means that the gamma transmission is normalized to that which would occur if the attenuation caused by the NW was zero (for the case of no gamma-attenuating material present in the NW). The partial attenuation according to the function a(q, t), which is a physical modulating function, is represented by the equations shown below.

$$a(q,t) = S_q^* + A_q \sin(\omega_q t + p_q) \qquad \text{Eq. 5a}$$
$$= S_q^* + A_q[(\sin\omega_q t)(\cos p_q) + (\cos\omega_q t)(\sin p_q)]) \qquad \text{Eq. 5b}$$
$$= S_q^* + (A_q \cos p_q)\sin\omega_q t + (A_q \sin p_q)\cos\omega_q t \qquad \text{Eq. 5c}$$
$$= S_q^* + A_q' \sin\omega_q t + A_q'' \cos\omega_q t \qquad \text{Eq. 5d}$$

In Eqs. 5, $S_q^*$ is referred to as the shift constant since it can move the a(q, t) function along the time axis, while $A_q$ is the amplitude of the a(q, t) function; $\omega_q$ is its frequency and $p_g$ is the delay, or phase-angle corresponding to the time delay $p'=p/\omega$. A variation in frequency, of course is inherent in frequency modulation (FM). The terms $A_q'$ and $A_q''$ are the combined amplitudes, formed by the product of $A_q$ with the indicated trigonometric functions of the phase angle. The structure of Eq. 5c shows that phase modulation (PM) is mathematically equivalent to a dual-amplitude modulation (AM). As an observation of Eq. 5a: when seeking an efficient and simplified design and operation of the modulation unit, the invention can be configured to work with more than one kind of modulation (such as FM or PM, rather than solely with AM), or designed to combine all three of these modulation modes in various ways.

After the completion of the modulation-encoding process performed in Step 3, in Step 4 of FIG. 10A, two kinds of fluxes travel toward the detector: (1) those fluxes from single-scattering within the inspected object and (2) fluxes unrelated to the inspected object density distribution.

Thus, in Step 4 of FIG. 10, the invention observes the single-scattered gammas that emanate from any representative jq-th voxel (from the j-th slice in the inspected object, and passing through the q-th NW of the modulating unit 120) before reaching the detector/spectrometer. The symbols below that are used in subsequent equations represent the following quantities:

- $\phi_{jq}$=the steady flux of single-scattered gammas having energy $E_j'$, incident on the q-th NW of the modulating unit; Eq. 2 also addresses such a flux.
- a(q, t)=the time-dependent attenuation function expressed by Eq. 5, imposed on the gamma flux incident on the modulating unit's NW #q.
- $A_D$=the geometrical unobstructed area of the detector as seen through the NW #q.
- $\alpha_q$=the angle of incidence of the gamma flux (measured between the trajectory of the gammas and the surface vector of the detector. This angle is zero for gammas arriving perpendicular to the plane of the areal surface of the NW #q.

The subscript q that encompasses indices I and k (as shown in FIG. 10) may be used in three respects: 1) to indicate those fluxes of gammas scattered from any among J isogonic slices within the inspected object, and pass through NW #q of the modulating unit; 2) to indicate a unique attenuation function a(q, t) of the $q^{th}$ NW; and 3) to specify the angle of incidence of the gamma flux at NW #q, as will be discussed shortly.

The following Eqs. 6a and 6b describe the periodically varying gamma stream having photons of energy $E_j'$ at the exit of window #q of the modulating unit, that reaches the detector due to the convergence of paths depicted in FIG. 9.

The relationship among the important count-rate and flux-related magnitudes may be demonstrated by the following example. The unknown constant local flux of single-scattered gammas $\phi_{jq}$, enters the modulating unit's NW. These gammas exit that NW at a somewhat reduced intensity given by the quantity $[\phi_{jq}a(q, t)]$. That term, when multiplied by the detector's area $A_D$, expresses the stream of modulated gammas leaving NW #q of the modulating unit and traveling in the direction of the detector/spectrometer. That product has to be multiplied by the detector efficiency $\eta_{jq}$. Dual subscripts j and q are used with this detector efficiency term to indicate its dependence on the gammas' energy, and on the NW's location in the modulating unit, respectively. That location also affects the incidence angle $\alpha_q$, of gammas arriving at the detector. Since the cosine of that angle specifies the fraction of the arriving gammas that will enter the detector, the following equation, encompassing all the listed parameters, expresses the detector count rate $D_{jq}'$, which corresponds to the local scattered gamma flux $\phi_{jq}$ and local mass density $\rho_{jq}$.

$$D_{jq}'=[\phi_{jq}A_D\eta_{jq}\cos\alpha_q][a(q,t)] \quad \text{Eq. 6a}$$

which equation contains the group $$[\phi_{jq}A_D\eta_{jq}\cos\alpha_q]=\Phi_{jq} \quad \text{Eq. 6b}$$

In Step 5 of FIG. 10B, the detector/spectrometer output signal is fed into the MCA 135 which sorts the detected signal pulses into bins, each corresponding uniquely to a particular scattered energy of the detected gammas. The invention can be configured so that a selection may be made in terms of bin width $\Delta E_j$, which defines energy resolution; the number of bins, and the full range of energy values to be covered may also be selected. In this application, the count rate $D_j'(t)$ of each bin varies periodically with time because gamma fluxes undergo temporal modulation during their passage through the NWs of the modulating unit.

Based on its constituents, the symbol $\Phi_{jq}$ represents the detector's response to unmodulated single-scattered gammas passing through any particular fully open NW #q. Once the value of such a response term is numerically determined, the matrix of flux values $\phi_{jq}$, that the system seeks, can be calculated from the matrix of these $\Phi_{jq}$ values defined above, since other parameters in Eq. 6b are known.

When $\Phi_{jq}$ is used in Eq. 6a, a convenient working form becomes:

$$D_{jq}'=\Phi_{jq}a(q,t) \quad \text{Eq. 6c}$$

The known function a(q, t) is retained as a term separate from $\Phi_{jq}$ within the $D_{jq}'$ term so that the invention can use the Fourier Transform involving the product $[a(q, t)\cdot b(n, t)]$ in the course of data processing.

In order to calculate the $\Phi_{jq}$-matrix, one proceeds by considering all the JN values of detector count rates corresponding to local gamma fluxes incident on the NWs of the modulating unit. Thus, the data processing may start from the measurable information, namely the sub-total count rates, such as D>, which are registered in the $j^{th}$ bin of the detector/spectrometer's MCA. That count rate, through $D_{jq}'$, encompasses the effects of all $\Phi_{jq}$ contributions. The relation of $D_j$ with its constituents, $D_{jq}'$, and with the total count rate D*, (that is formed by the summation of all J sub-total count rates $D_j$), is given by the following two equations:

$$D_j = \sum_{q=1}^{N}\Phi_{jq}a(q,t) + \sum_{q=1}^{N}\varphi_j' = \sum D_{jq}' + \varphi_j' \quad \text{Eq. 7}$$

$$D^* = \sum_{j=1}^{J}D_j \quad \text{Eq. 8}$$

The $2^{nd}$ summation term in Eq. 7 is expressed by the abbreviated symbol $\Phi_j'$, that encompasses gamma fluxes $\phi_j'$ of energy $E_j$, which are traveling toward the detector and are unrelated to the inspected object's internal density distribution. These gamma fluxes might undergo multiple or single scattering wherein at least one of the scattering events occurs external to the inspected object; some of those fluxes are due to background radiation. The physical reality is that the group of registered gammas, denoted by $\Phi_j'$, contains fluxes that may have been scattered randomly one or more times in various objects and at various distances from the detector. They include the following radiation components:

un-modulated single-scattered gammas from portions of the isogonic shell external to the isogonic slices (external to the inspected object).
  multiply-scattered (modulated and un-modulated) gammas, as well as background radiation of various origins.

All of the radiation components listed here may have an energy $E_j'$, and therefore will be registered in the $j^{th}$ energy bin of the MCA 135. However, none of the undesired components yields useful information on the inspected object's density field. All of these signals have no systematic time-variation; but their magnitude could either be measured separately or calculated. In the latter option, they can be subtracted from the bin-registered count rate $D_j$; also they could be mathematically eliminated during the data analysis. The recommended data processing incorporates application of the Fourier Transform.

In condensing information given earlier on the modulation of fluxes, it is observed that, as a consequence of the modulating unit's design, directional orientation, and operation, gamma fluxes incident upon NWs of the modulating unit may become appropriately encoded while passing through the modulating unit's NWs; such encoding makes possible the determination of the following:

In the first operation, the $\Sigma D_{jq}'$ summation term, seen in Eq. 7 is important for further data processing, because it includes all the useful single-scattered gamma fluxes—contained in the $\Phi_{jq}$ terms—pertaining to the scattering occurring in the $j^{th}$ isogonic slice within the inspected object. These slices are important because only detected gammas which scatter once within such slices carry the signature of the gamma flux and mass density distribution within the inspected object. Also, as indicated earlier, J of these virtual slices fill the volume of the inspected object.

Individual count rate-related terms are $\Phi_{jq}$, from Eqs. 6b and 7, which terms were included within the directly-measured $D_j$ term. $\Phi_{jq}$ corresponds to gamma flux components $\phi_{jq}$ incident on the modulating unit's NWs, where each component of gamma flux is associated with a particular jq voxel of the inspected object. This second operation of determining all (N) of the needed local magnitudes $\Phi_{jq}$ is expanded to all J isogonic virtual slices, resulting in the determination of (JN) such terms, covering the entire inspected object's internal scattered gamma flux-distribution. This distribution is subsequently converted into the three-dimensional mass (density) distribution and a corresponding computerized visual image.

In Step 5 of FIG. 10B, the set of output signals from the MCA are split into J sets of signals. Because of the Compton scattering energy-angle relationship defined in Eq. 1, the sorting of output signals from the detector based on their energy also becomes a sorting by scattering angle $\theta$. In the MCA bin #j, the energy $E_j'=E'(\theta_j)$ of scattered gammas is associated with the registered gamma counts $D_j(t)$ in that particular energy bin.

The count rate registered in each energy bin should be processed N times (where N is the maximum value of q, thus defining the total number of NWs in the modulating unit). Therefore, N is also equal to the number of unknown scattered fluxes to be determined (emanating from N voxels in the j-th isogonic slice of the inspected object); these fluxes are incident upon the modulating unit. Consequently, as illustrated in Steps 6 and 7 of FIG. 10B, each of the J sets of $D_j(t)$ signals is further split into N equal signals by a signal splitter, and sent to N multiplying black boxes shown in Step 7. For the $1^{st}$ signal-splitting level performed in Step 5, input signals for each signal splitting box differ from input signals for other signal splitting boxes. However, for each particular ($j^{th}$) signal-splitting box of Step 6, all the split signals exiting any of these individual boxes are identical among themselves. The latter group of equal split signals from the j-th box, of course, differs from groups of signals exiting other similar boxes where the subscripts has a different value. Such signal-splitting enables the concurrent processing of all measured counts. While the following analysis and derivations are outlined based on a representative $j^{th}$ value of the energy of scattered gammas, they are fully applicable to any other energy value of scattered gammas.

In Step 7, a set of time-varying b(n, t) sine functions are electronically generated by a function generator 182. In this stage of the process, the invention introduces a new dimensionless transform-function, denoted in its general form as $F_b(n, t)$. The term "transform" refers to this function's role in performing the Fourier Transform that will be outlined below. The transform function has to be selected to match the modulating function a(q, t), expressed in Eq. 5, as is done by the example of a specific function $F_b(n, t)$, given by Eq. 9.

$$b(n,t)=B_n^* + B_n' \sin \lambda_n t + B_n'' \cos \lambda_n t \qquad \text{Eq. 9}$$

The above function b(n, t) mimics the a(q, t) function from Eq. 5. The transform function b(n, t) serves as a time-dependent multiplier of the detector output signal $D_j(t)$, as will be shown later in Eq. 11. The above transform function represents the n-set (where n is a positive integer, taking values from n=1, to n=N) of periodic oscillations, mathematically similar to the q-set of the a(q, t) functions. The gamma flux modulating functions a(q, t) are physically generated by the time-dependent attenuation of the modulating unit. On the other hand, transform functions b(n, t) are electronically-generated digital functions. One noted difference between the a(q, t) functions and the b(n, t) functions is that in the b(n, t) function, there is no need for a separate reference to the phase-lag addressed in the earlier discussion of the a(q, t) function in Eq. 5. Also, within the b(n, t) function an operator can choose and vary the values of parameters such as the shift constant B* and amplitudes B' and B" by computer control (in some solution procedures, one or more of the listed B-coefficients might be chosen to be zero or one). To the contrary, the operator can vary the hardware-related A-parameters of the a(q, t) function only by changing the NW and attenuator configuration of the modulating unit.

The circular frequencies $\omega_q$ and $\lambda_n$ appearing in functions a(q, t) and b(n, t), respectively, are defined to assume only discrete values, appropriate for the application of the Fourier Transform. These frequencies obey the relationships defined in Eq 10:

$$\omega_q = \pi q^*/T, \text{ with } q^* = f_q(q) \text{ or } f_i(i) \text{ incorporated in } a(q,t) \qquad \text{Eq. 10a}$$

$$\lambda_n = \pi n^*/T, \text{ with } n^* = f_n(n) \text{ with } \lambda_n, \text{ incorporated in } b(n, t) \qquad \text{Eq. 10b}$$

$$\text{Also, } n^* \text{ can be expressed as: } n^* = f_i(i) \text{ or } n^* = f_q(q) \qquad \text{Eq. 10c}$$

The use of functions $f_i$, $f_n$, and $f_q$, as choices in the group of Eqs. 10 depends on the analysis approach selected, as will be shown in Steps 8 and 9 of FIG. 10B. The parameters (i, n, n*, q and q*) shown above are positive integers; their selected values also depend on the analysis approach. For i, the maximum value is I, while for both n and q the maximum value is N. T is the half-period of the oscillation of the slowest moving attenuating element in the modulating unit (for which element q*=1).

In Step 7, the MCA output is multiplied by the $2^{nd}$ set of temporal functions b(un, t), generating a product [$\Phi$(q)·a(q, t)·b(n, t)]. Both of these functions—a(q, t) and b(un, t)—are chosen to be periodic (sine or cosine) functions. In this and the following analytical operations, depicted by Eqs. 11 through 13 below, products of functions, including a(q, t) and b(un, t) are formed and integrated over time. Referring to FIG. 10B, the small black boxes (shown in Step 7) represent electronic devices in which digital signals from the J signal splitting boxes 180 are joined by digital signals from the b(un, t)-function generator 182. In these black boxes, the two signals are multiplied with each other. In other words, the time-dependent MCA output signal $D_j(t)$ from energy bin #j is multiplied in each branch by one electronically-generated function b(n, t), forming a combined signal. In the next parallel branch, the same signal $D_j(t)$ is multiplied by another function b(n, t) with a different set of values for n-dependent and n-subscripted parameters introduced in Eq. 9.

Since both factors [$D_j(t)$ and b(n, t)] of the product term are functions of time, their product-function is also time-dependent. The integration of the product function, in Step 8, constitutes a version of the Fourier Transform. These products are integrated over a period of time, as in a Fourier Transform, to eliminate signals other than those generated by the single-scattered gamma photons originating in the inspected object, and modulated by the modulating unit. According to Eq. 13 in Step 8 of FIG. 10B, such product functions are then integrated by an integrator 184 over a selected measurement-time period that may be equal to T, or preferably any integral multiple of 2 T. Such an integration is an important step in the subsequent decoding of the gamma fluxes, wherein their original encoding was accomplished within the modulating unit by the time-dependent attenuation function a(q, t).

The detector count rate, as its response to a modulated flux of local single-scattered gammas, is given by Eq. 6a. The corresponding flux group from Eq. 6b of scattered gammas had a constant magnitude $\Phi_{jq}$ (independent of the modulation), and the gammas comprising that scattered flux have modulation-independent energy $E_j'$. The count rate $D_{jq}'$ is also expressed by Eq. 6c, which is the detector response to single-scattered gammas of energy $E_j'$ incident on the $q^{th}$ NW.

Using Eq. 7 for $D_j(t)$ and Eq. 9 to express b(n, t), the product [$D_j(t)$ b(n, t)] may be expressed as:

$$D_j(t) \cdot b(n,t) = D_j(t) \cdot [B_n^* + B_n' \sin \lambda_n t + B_n \cos \lambda_n t]$$  Eq. 11

Substituting the expression for $D_j(t)$ given in Eq. 7 yields:

$$D_j(t) \cong b(n, t) = \left[\sum_{j=1}^{N} \Phi_{jq} a(q, t)\right][b(n, t)] + [\Phi_j'][b(n, t)]$$  Eq. 12

The $\Phi_j'$ term in Eq. 12 was expressed earlier in Eq. 7, as being without a time-variation imposed by the modulator. Since it is constant in time, upon integration within limits specified in Eq. 13a below, that term is eliminated, and therefore does not appear in Eq. 14. It should be noted that, while all terms in Eq. 12 become known or eliminated, only one category of terms remains unknown—the gamma flux terms $\Phi_{jq}$. In order to determine each of these terms, the procedure is as follows: first, Eq. 12 is integrated between the selected finite integration limits (0 and 2 T), as expressed by Eq. 13a below, which applies to any value of j. With functions a(q, t) and b(n, t) substituted in Eq. 12 by their expressions in Eq. 5d) and Eq. 9, respectively, the resulting Eq. 13a reads as follows:

$$\int^{2T} D_j(t) b(n, t) dt =$$  Eq. 13a $$\sigma_{jn} = \int^{2T} D_j(t)[B_n^* + B_n' \sin \lambda_n t + B_n'' \cos \lambda_n t] dt$$

The term $\sigma_{jn}$ is the result of the Fourier Transform of the count rate from bin #j, encompassing gamma fluxes having an energy associated with that bin.

Now, substituting the expression for $D_j(t)$ in the above integral by using Eq. 12 and using $B_n^*=0$ (for simplification) for each particular value of n in the b(n, t) function, results in:

$$\sigma_{jn} = \int_o^{2T} \left\{\left[\sum_{q=1}^{N} (\Phi_{jq})(S_q'' + A_q' \sin \omega_q t + A'' \cos \omega_q t) + \Phi_j'\right][B_n' \sin \lambda_n t + B_n'' \cos \lambda_n t]\right\} dt$$  Eq. 13b Since the quantity $\sigma_{jn}$ as expressed in Eq. 13a is the integral of known functions within a selected finite limit of time (the duration of the inspection measurement wherein gamma counts are recorded), the symbol ($\sigma_{jn}$) represents a known, calculated number. For a defined set of recorded data, that number depends only on the values of coefficients and frequencies associated with the parameters q and n, the former within the function a(q, t) and the latter within the b(n, t) function that is given by Eqs. 5 and 9, respectively. On the other hand, since N unknown constant groups $\Phi_{jq}$ (proportional to NW-incident scattered fluxes) appear in Eq. 13b, when n is varied from 1 to N, each value of n generates an equation of the type Eq. 14 that is linear in regard to $\Phi_{jq}$. In Step 9 of FIG. 10B, the output of the integrators 184 results in a system of N linear algebraic equations, providing N values of the local gamma flux at each of the N voxels within the j-th isogonic slice of the inspected object. In this manner, the decoding of the modulated fluxes is achieved in all (JN) voxels of the inspected object. When equations of the Eq. 14 type are mutually independent, they represent a system of linear algebraic equations 186 which can be solved for the unknown incident fluxes by an equation solver.

With the integrations performed, as indicated in Eq. (D-5b), the result reads:

$$\sigma(j, n) = \sigma_j(T) =$$  Eq. 14

$$\left\{\sum_{q=1}^{N}\left[\Phi_{jq} \int_o^{2T} a(q, t) \, b(n, t) \, dt = \left\{\sum_{q=1}^{N}[(\Phi_{jq})(T \; C_{nq})]\right\}\right.\right.$$

where:

$$C_{nq} = (A_q' B_n' + A_q'' B_n'')$$

In the above equation, all NWs of the modulating unit 120 are included through the indicated q-summation, starting with q=1 and ending with q=N, since N is the total number of these windows in the modulating unit. The shape or form of the NWs is not a condition for achieving a solution.

Eq. 14 above represents in a condensed form, a system of N linear algebraic equations, utilizing values of the parameter σ(j, n) for each value of the index n (which starts with the value 1 and ends with N), while the span of values of the index j is from 1 to J.

The solution of linear algebraic equations (for a variety of design and operation options of the modulating unit) is indicated in Step 9 of FIG. 10B. The application of Eq. 14 for a system with N unknown fluxes results in a system of N independent linear algebraic equations and is illustrated by Eq. 15 shown in FIG. 11. For any particular chosen $j^{th}$ energy of scattered gammas, that equation represents, in an abbreviated manner, the complete set of N linear algebraic equations, with the same number N of unknown values of the local single-scattered gamma flux group $\Phi_{jq}$.

Eq. 15, as shown in FIG. 11, results from expanding Eq. 14 for a given j-value, but with various values of n and q, yielding the illustrated set of N linear algebraic equations. This system of equations can be solved for all values of the parameter $\Phi_{jq}$ that is (according to Eq. 6b) proportional to the value of the local gamma single-scattered flux—eventually resulting in a determination of flux and mass density distribution within the inspected object.

In Step 9 of FIG. 10B, the field of single-scattered gamma fluxes is determined for the entire inspected object—by combining solutions of J systems of equations such as Eq. 15 into a numerically-determined (known) spatial matrix. Subsequently, in Step 10 of FIG. 10B, the density field is reconstructed within the inspected object by converting the local gamma fluxes into densities. It is noted that the detected signal incorporates the cumulative effect of local scattering and two sets of density-related attenuation: 1) along the gamma beam path (axis) from the source to the scattering point, and 2) along the gamma path from the scattering point to the detector. Each attenuation depends on the average density distribution along their respective axes. That distribution, as it becomes known, enables the image reconstruction using this invention.

Density Field Reconstruction

In step 10 of FIG. 10B, the density field within the inspected object is reconstructed by a three-dimensional density field reconstructor 188 by converting the local gamma fluxes into local densities. The two average densities appearing in Eqs. 2 and 3, in turn, depend on the unknown density distribution along their respective axes. Consider any material inside the inspected object. An unambiguous correspondence exists between the three-dimensional distribution of local single-scattered gamma fluxes and the three-dimensional distribution of material densities that represent the density image. The term "local single-scattered gamma fluxes" pertains to gamma photons originating within voxels associated with scattering points within the inspected object. The unambiguous correspondence between gamma flux and material density is illustrated in Eqs. 2, 3, and 4, in which the field parameter "kappa"—written with the subscript P (denoting point of scattering) instead of the indices jq—combines several terms. The rewritten Eq. 4 reads:

$$\kappa_P = \phi_{jq}/[(Q^*K_{jq}^*)(G^*P'')_{jq}] = \rho_P \rho_o P_P' \quad \text{Eq. 16}$$

At the beginning of the field-conversion effort, the JN numerical values of the following parameters are known:
- the terms $\Phi_P$, from Eqs. such as Eq. 15 (FIG. 11).
- local fluxes $\Phi_P$ which are related to $\Phi_P$ by Eq. 6b.
- the parameter $\kappa_P$, calculated from the fluxes $\Phi_P$ and known parameters, using Eq. 16.

Having available the necessary number of numerical values of the parameter $\kappa_P$, Eq. 18 must be applied (JN) times, which number was shown to be the total number of unknown local densities $\rho_{jq}$, as shown in Eq. 17 below. In Eq. 17, the flux-to-density field conversion becomes simpler when the integrals included in the probabilities of non-attenuation (from Eq. 3) are expressed as sums of local, voxel-related densities $\rho_{jq}$.

$$\kappa_P = [\rho_P]/\exp\left\{\left[k_o \sum_{j=j_S}^{j=j^*} (\rho_{jq})_o \Delta r\right] + \left[k_P' \sum_{j'=j_D'}^{j'=j^*-1} (\rho_{jq}')' \Delta h\right]\right\} \quad \text{Eq. 17}$$

The above equation incorporates the field parameter κ and the local density ρ, the latter in two functional forms: as $\rho_P$ and summed-up values $\rho_{jq}$. In further derivations and figures, the directions $r_q$ and $h_q$ will be often denoted only by q and q' respectively.

Equation 16 illustrates how to calculate numerical values of $\kappa_P$ at any of the scattering points P, associated with gamma flux values $\phi_{jq}$, which are already numerically determined at all the scattering points within the inspected object. Other parameters and variables with the symbol and subscript (P), including the density $\rho_P$, also pertain to scattering points 122 in FIGS. 1 and 12, identified by the symbol SP or P. The cited coordinates and other parameters are listed appropriately and indexed/subscripted or otherwise marked; they are also shown in FIG. 12.

Figure 12:
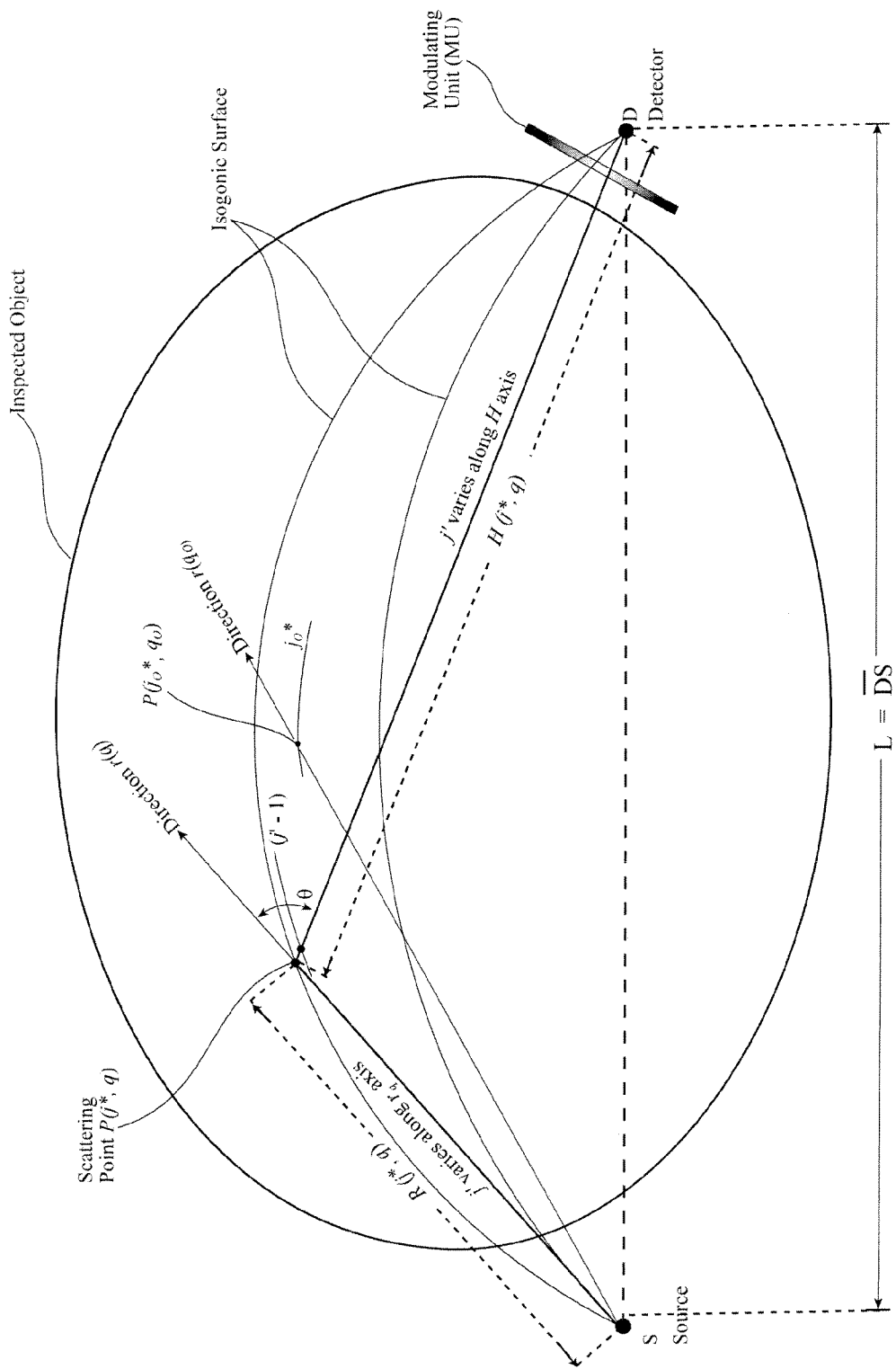
FIG. 12 illustrates parameters relating scattered gamma photon flux to mass density within the inspected object.

The deployment of the key components of the invention (source, modulator, and detector) shown in FIG. 12 places the modulator between the inspected object and the detector. The analysis provided below for reconstructing the mass density within the inspected object is based on this arrangement. An alternate arrangement of the key components would be for the modulator to be placed between the source and the inspected object. The data analysis for that alternate arrangement is analogous to the first arrangement and utilizes the same input data, mathematical solution, and data processing.

As illustrated in FIG. 12, the location of the point P in a plane cross-section through the inspected object is defined by two indices (j* and q), employed as follows: The index j* defines the particular isogonic slice on which point P is located (the slice being associated with the energy $E_j'$ of the scattered gamma), while q axis—by intersection with the j* curve—defines the location of point P on the isogonic slice. That location (inside the inspected object) is associated with the virtual projection along the corresponding axial direction #q onto the isogonic slice, as observed from the point S (Refer to FIG. 12. The coordinates (j, q), and their above-listed specific values (e.g., j*, j', $q_D$, and q) utilized in FIG. 12 and in Eqs. 17 and 18, help illustrate how gamma photons that are scattered from the isogonic slice #j*, pass across a number of other isogonic slices (associated with the variable subscript j') on their way from point P while traveling in the direction h(q') toward the modulating unit and the detector D. Regarding other notations in Eqs. 17 and 18 to follow, $k_o$ pertains to the attenuation of gammas having a source energy $E_o$, as in Eq. 3a, and $k_P'$ is the attenuation probability, depending on the energy $E'(\theta_P)$ of scattered gammas, addressed earlier in Eq. 3b.

In Eq. 17, the subscript "o" with the parenthesis around the density term $\rho_{jq}$ of the first summation, and the prime symbol with the second summation, have the meaning associated with these symbols when specifying $k_o$ and k', as explained earlier in Eq. 3. In Eq. 17, these two symbols signify that different sets of local densities—$(\rho_{jq})_o$ and $(\rho_{jq})'$—are summed up along two distinct axes, the r-axis (from the source), and the h-axis (from the SP), respectively. Such a distinction applies to real systems, with non-uniform density distributions, wherein densities may vary differently along these two axes. Thus, for the modulator unit located near the detector, in accordance with FIG. 12 and the explained application of subscripts j and q, it is evident that j varies along the r-axis (direction q for the primary gammas) in a different way from the variation of j' along the h-axis that is denoted by h(q) for the scattered gammas. Thus, Eqs. 17 and 18 can be so formed to cover all JN scattering points in the inspected object, thus enabling the calculation of all JN local densities at these points, based on the JN local fluxes that were already calculated.

In order to obtain a numerical solution, Eq. 17 is converted to the logarithmic form shown below as Eq. 18, to simplify the numerical operations by working with a linear form of most of the unknowns rather than with their exponentials:

$$\ln \kappa_P = \ln \rho_P - \left\{ \left[ k_o \Delta r \sum_{j=j_S}^{j=j^*} (\rho_{jq})_o \right] + \left[ k'_P \Delta h \sum_{j'=j'_D}^{j'=j^*-1} (\rho''_{j'q})' \right] \right\}$$

In multiple applications of the above equation, the subscript P pertains to values of $\kappa$, $\rho$, and k' at coordinates (j*, q) of point P. There are JN total variations of the two coordinates of the points P in the volume of the inspected object, wherein each of the points P, identified by the coordinates (j*, q) represent a specific voxel. Thus, the total number of voxels under consideration within the inspected object is also equal to the product JN.

In order to transform the flux field of scattered gammas into a mass density field, Eq. 18 has to be solved for the local densities in JN voxels (i.e., at JN points P). The sequence for the successive selection of points P, i.e., for conducting the numerical calculations is left to the user's discretion. Among available choices, the points P along the inspected object's isogonic slices can be varied, or the user can start in one section of the inspected object (moving spirally or otherwise inward or outward), and then switch to other sections; or the user may conduct the numerical operations by other paths and sequences. Since the complete system of JN equations is simultaneously solved, the described field reconstruction method need not be applied in steps, such as to a succession of cross-sections of the inspected object (as used in image reconstructions for CAT and MRI applications), which require multiple axial positionings of the measuring system relative to the inspected object.

A portion of the densities $\rho_{jq}$ and $\rho'_{j'q}$ is summed-up in each local application (at each scattering point P) of Eq. 18. As in FIG. 12, with the variation of locations of the point P, at least one of the two axes (r and h) also vary. Therefore, a limited but varying number (batch) of densities $\rho_{jq}$ is included in each direction of the gamma path through the inspected object, for each application of Eq. 18. The contents of such batches of densities differs for different scattering points since each pair of axes r and h cover only a fraction of the inspected object's volume. The number of densities in each batch is less than JN, but each particular density out of their total number JN appears in one or more batches, i.e., one or more equations of the type Eq. 18. Accordingly, the user has available a solvable system of JN independent, albeit non-linear, equations of the form shown by Eq. 18. Therefore, the established system of JN equations can be used for the numerical determination of the same number JN of unknown local densities. It is noted that the form of Eq. 18 is very similar to that of a linear algebraic equation, except for only one logarithmic term.

Eq. 18 may be written as the system of JN equations shown below, using the subscript scheme from FIG. 12. The subscript P is replaced by the actual pair of subscripts (j* q) defining a three-dimensional matrix of scattering points, since q is a two-dimensional index. The following equation set is designated as Eq. 19.

For (j*, q)=(4, 1) and q'=5', at point A of FIG. 12 yields:

$$(\ln k)_{4,1} = \ln \rho_{4,1} - k_o \ \Delta \ r \ \rho_{1,1} - k_o \ \Delta \ r \ \rho_{2,1} - \qquad \text{Eq. 19a}$$
$$k_o \ \Delta \ r \ \rho_{3,1} - \ldots - k' \Delta h \ \rho_{3,5'} - k' \ \Delta h \ \rho_{2,5'} - k' \ \Delta h \ \rho_{1,5'}$$

In like manner, for (j*, q)=(5, 1) and q'=6', at point B yields:

$$(\ln k)_{5,1} = \ln \rho_{5,1} - k_o \ \Delta \ r \ \rho_{1,1} - k_o \ \Delta \ r \ \rho_{2,1} - k_o \ \Delta \ r \ \rho_{3,1} - \qquad \text{Eq. 19b}$$
$$\ldots - k' \ \Delta h \ \rho'_{4,6} - k' \ \Delta h \ \rho'_{3,6} - k' \ \Delta h \ \rho'_{2,6} - k' \Delta h \ \rho'_{1,6}$$

And for (j*, q)=(6, 1) and q'=7', at point C yields:

$$(\ln k)_{6,1} = \ln \rho_{6,1} - k_o \ \Delta \ r \ \rho_{1,1} - k_o \ \Delta \ r \ \rho_{2,1} - k_o \ \Delta \ r \ \rho_{3,1} - \qquad \text{Eq. 19c}$$
$$\ldots - k' \ \Delta h \ \rho'_{5,7} - k' \ \Delta h \ \rho'_{4,7} \ldots - k' \ \Delta h \ \rho'_{1,7}$$

The sub-set of Eqs. 19 above illustrate the relationship of the density parameter with other variables (that are known or can be measured or calculated) along the q=1 axis and for any values of j* and q'. Staying with one q-value, j* is varied between its extreme values inside the inspected object.

Now, in the next sub-set of equations, j*=4, but the r(q)-axis is moved to the left where q=2, so that the (j*, q) intersection at point E is along the direction h(q') from the detector, with q'=5'. In this way, point F is identified by j=3 and q=1, having the same coordinates j=3 and q'=4'.

Continuing, for (j*, q)=(4, 2) and q'=4', for point E yields:

$$(\ln k)_{4,2} = \ln \rho_{4,2} - k_o \Delta r \rho_{2,1} - k_o \Delta r \rho_{2,2} - k_o \Delta r \rho_{3,2} - \ldots$$
$$-k'\Delta h \rho_{3,4'} - k'\Delta h \rho_{2,4'} - k'\Delta h \rho_{1,4'}$$

For the new value of q=(2, j*) is to be varied further, analogous to its variations for q=1.

Figure 13:
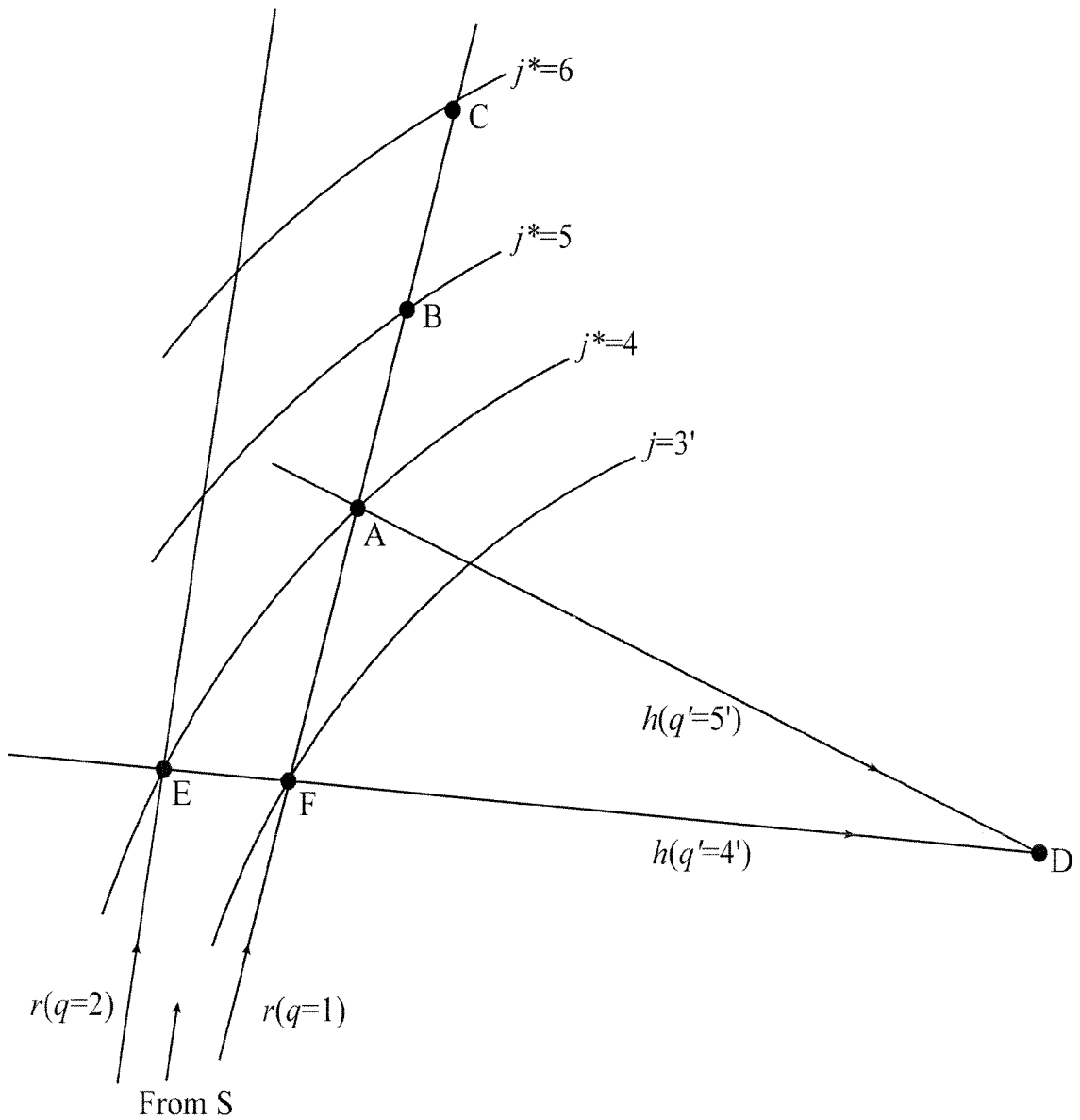
FIG. 13 illustrates parameters used in density reconstruction.

Referring to the third term in the top equation (for point A) of the above set of equations, and the fifth term in the last equation (for point E) of the set, according to FIG. 13, $\rho$(j, q)=$\rho$(3, 1)=$\rho$(3, 4') since both notations indicate point F. The different second index is used to distinguish between summation along the r(q) and h(q') axes, which axes bear numbers (r=1) and q'=4'), respectively. The importance of the same density appearing in the format illustrated above is in its different multipliers: the term $k_o \Delta r$ is not equal to the term $k'\Delta h$. This difference assures the non-proportionality of the rows and columns in the system of equations—a necessary condition for the system of equations to be solvable. There are several approaches available for solving the set of JQ equations, as outlined below:

Approach I—Since the Eq. 19 set has JN independent equations containing the same number of unknowns, despite its mixed (algebraic plus logarithmic) form, that set of equations has only one set of JN values of p as its exact solution. Any set of JN equations (whether algebraic or transcendental)

with JN unknowns is solvable. Eq. 19 consists of mostly algebraic terms; only the first term (the logarithmic term) is transcendental. The set of equations may be solved algebraically to a first approximation, particularly since the (ln ρ)-values are an order of magnitude smaller than the (ρ)-values. Further iterations in the solution can then account accurately for the (ln ρ) contributions.

Approach II—The above system of equations becomes a linear set when the ln ρ and ρ terms for each point P are temporarily considered to be independent unknowns within the inspected object, thus doubling the number of unknowns. But all of them can be numerically determined from the linear algebraic equation system when another set of JQ independent measured information is utilized. That set consists of the measured flux of scattered gammas and their κ-values for points along the system's boundary. Then, it is easy to calculate values of local ρ and their logarithmic values. When the consistency of such calculated values is checked, any discrepancies can be reduced by iteration, or use of the least squares method.

Approach III—Analogous to Approach II, instead of increasing the number of equations, the number of unknowns could be reduced, omitting every other density. This is equivalent to a density value expressed as the average value of two adjacent densities. In that way, the number of equations and unknowns will be matched. If needed, iterations based on such calculated local densities can improve the accuracy of the results.

Approach IV—Another solution approach is to normalize Eq. 17 so that each density term is replaced by a density ratio close to unity. Then, the logarithmic term in Eq. 18 may be expressed by a Taylor Series, so that a non-linear, but algebraic system of equations remains to be solved. This approach requires less computing time than for the case of an equation system that incorporates both logarithmic and algebraic terms. Further, iterations may be performed to increase the accuracy of the results.

Measurement of Density Distributions of Multiple Materials in an Object

The invention may be used to determine the three-dimensional density distribution of individual multiple materials in an inspected object by adding a multiple number of gamma source energies, or positioning the detector or gamma source in a multiple number of different positions, or a combination of those alternatives. An illustration of how this is accomplished is provided below.

Consider an object made of two materials (U=2) having different densities $\rho_A$ and $\rho_B$, distributed in an unknown manner throughout the inspected object. It is recognized that the composite density at any point in the object is the sum of the component densities $\rho_A$ and $\rho_B$. Using the invention as described earlier, the object is irradiated by a gamma source having two different energies, $E_1$ and $E_2$. The invention is operated as described earlier, and data is recorded separately for irradiations by each of the gamma fluxes having photon energies at $E_1$ and $E_2$. The analysis of the two sets of data is conducted as before, up to Eq. 18. This equation is then written to incorporate the sum of two density fields, reflecting contributions of the two densities, as shown in Eqs. 20 and 21 below, where subscripts 1 and 2, with Λ, k, and k' pertaining to the two cited source energies.

$$\ln \kappa_1 (j^*, q, U = 2) = \ln[\rho_A (j^*, q) + \rho_B (j^*, q)] - \left\{ \left[ \sum_{j_s}^{j^*} k_{oA} \, \rho_A (j, q) + k_{oB} \, \rho_2 (j, q) \right] \Delta r + \sum_{j'_D}^{j^*-1} k_{1A} \, \rho_A (j', q') + k_{1B} \, \rho_B (j', q') \right] \Delta h \right\} \quad \text{Eq. 20}$$

and $$\ln \kappa_2 (j^*, q, U = 2) = \ln[\rho_A (j^*, q) + \rho_B(j^*, q)] - \left\{ \left[ \sum_{j_s}^{j^*} k_{oA} \, \rho_A(j_1, q) + k_{oB} \, \rho_B(j, q) \right] \Delta r + \sum_{j'_D}^{j^*-1} k_{2A} \, \rho_A(j', q') + k_{2B} \, \rho_B(j', q') \right] \Delta h \right\} \quad \text{Eq. 21}$$

Since for U=2 materials (components) in the inspected object, one has available 2JN values of the parameter κ, the same number of equations of the above type can be formed. That number of equations is equal to the number of unknown local densities (JN for substance #A, and JN for substance #B), assuring the system's ability to solve for the two sets of unknown densities.

This example may be extended to a multiple number of source energies $U_{SE}$, a multiple number of source locations $U_{SL}$, and a multiple number of detector locations $U_{DL}$. Since two or more sources of different energy may be placed at the same location, the number of source locations $U_{SL}$ is always less than or equal to the number of source energies $U_{SE}$. Using the number $U_S$ to incorporate all the source-related variations (of location and energy) the product ($U_S \cdot U_{DL}$) indicates the number of equations available for solution, and also corresponds to the maximum number of unknown densities for which a solution may be obtained.

Accordingly, the invention may employ either $U_{DL}$ detectors, each of which is at a distinct location, and/or $U_{SE}$ gamma sources of the same energy, each of which are at a distinct location. One location may be selected to house multiple sources of different energies. In such a case, these sources (albeit at one location) are counted as separate items within the parameter $U_S$. Also within that number are counted all the different locations where sources of any energy might be placed. Thus, the variation in source energies is equivalent and additive to the variation in source locations, making $U_S$ a combined number of source locations and energies. Therefore, the total number of source locations $U_S$ can be equal to or smaller than $U_{SE}$. The required number of modulating units (situated either in front of the detector or in front of the source) is equal to the smaller of the two parameters $U_{SL}$ and $U_{SE}$.

Alternate Applications of the Modulating Unit

Further, in an alternate embodiment of the invention, the modulating unit may be configured in a three-dimensional geometrical arrangement, that can be serial—encoding the same streams of radiation in a serial manner—or they can be separate, e.g., one modulating unit encoding source radiation and the second modulating unit encoding the radiation immediately before it reaches the detector. In any of these, as well as other designs and applications of multiple modulation units, each of the modulating units includes its own particular set of attenuators, and may operate either independently or synchronously with the other modulation units.

Apart from the applications discussed earlier in this document, the modulating unit may be used in conjunction with any other gamma flux measurement in which it is desired to image the object from which the gammas emanate. The modulating unit may be inserted in the path of the gammas, between the inspected object and the detector, to encode the cross-section of the gamma flux with a unique periodic oscillatory attenuation in each of the NWs. This encoding provides a tag indicating the origin of each gamma photon within a two-dimensional cross-section of the inspected object. Depending on the design of the measurement system, this may be converted to yield three-dimensional spatial information within the object by using some form of scanning of the gamma source or the detector.

Stationary Inspection System for Three-Dimensional Imaging Employing Electronic Modulation of Spectral Data from Compton-Scattered Gammas In various exemplary embodiments, the inspection system can be implemented without a mechanical modulator to encode the scattered gammas. This simplified configuration, as shown, for example in FIG. 14, may consist of a mono-energetic source of gamma radiation and a detector-spectrometer—both of which can be stationary. The encoding of the detected scattered gamma signal can be accomplished electronically—by subjecting each of the upper and lower limits of the energy bins of the pulse-height analyzer (that sorts the detected photon signals, according to the energy of the photons) to a specific unique oscillatory change in voltage—corresponding to the related oscillatory change in detected photon energy. These oscillations in the pulse height analyzer energy bin boundaries result in oscillations in the virtual isogonic surfaces created by the combination of the Compton energy-angle relationship and the encoding produced by these oscillations. Namely, in this approach, modulation of the energy bin boundaries within the pulse height analyzer results in an encoding of the detected scattered gamma signal in this embodiment of the inspection system.

The inspection system can include a mono-energetic gamma radiation source 1405 and a detector-spectrometer 1410—both stationary with respect to each other and to the inspected object. The mono-energetic gamma radiation source 1405 may be partially contained within a radiation shield 1400. This system is similar to the system described above, but does not employ a mechanical modulator. The mono-energetic gamma source 1405 and the gamma detector-spectrometer 1410 can be approximated as point-size components. Mono-energetic gammas having energy E from the source 1405 irradiate the inspected object 1405 as previously described, but without the modulator].

Figure 14:
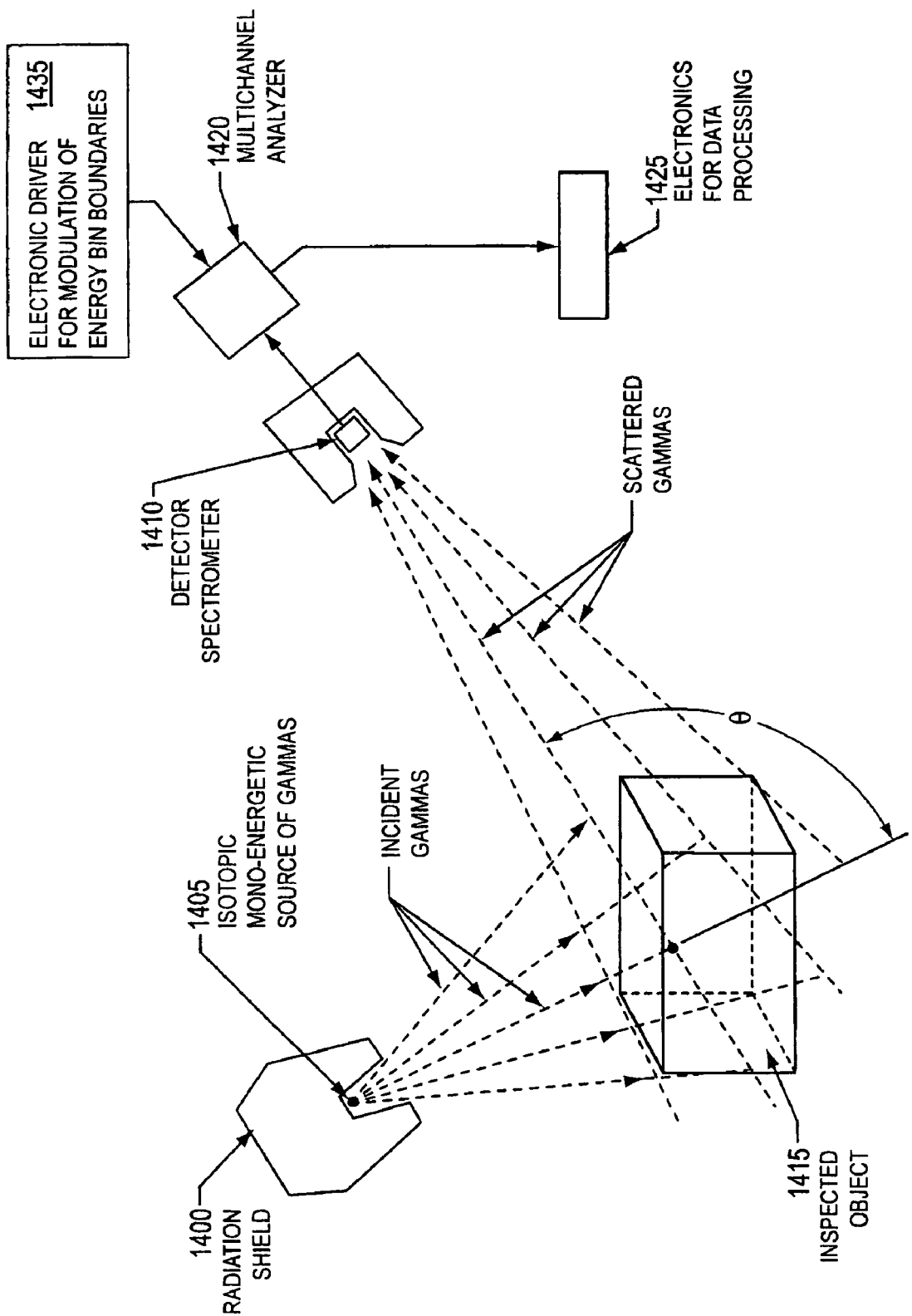
FIG. 14 depicts another exemplary embodiment of an inspection system according to the present teachings.
Figure 15:
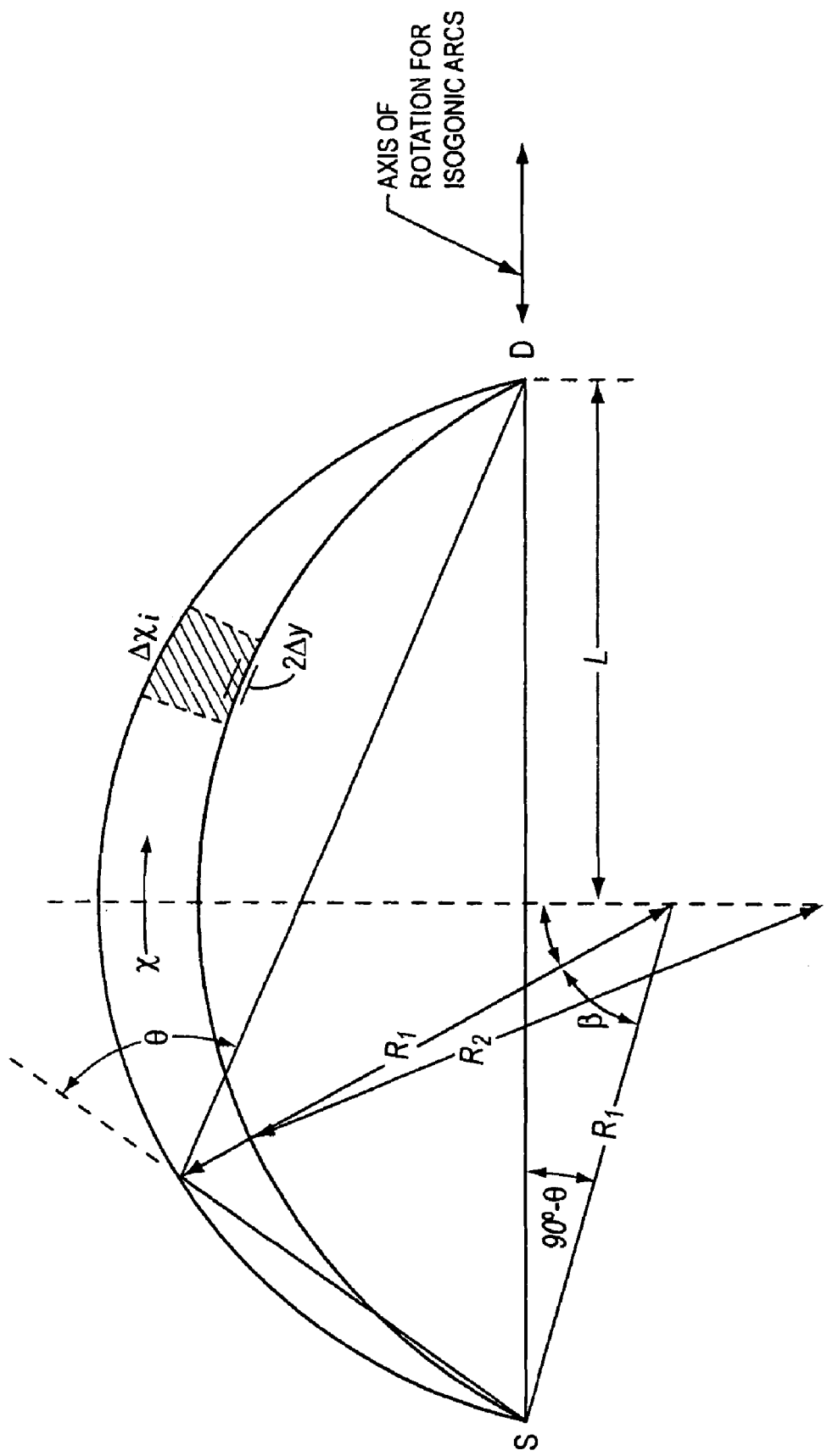
FIG. 15 is a two-dimensional illustration of the geometry of isogonic arcs associated with Compton scattering of gammas through an angle θ in accordance with the inspection system shown in FIG. 14.

As shown in FIG. 14, the output signals from the detector-spectrometer 1410 are sent to a multi-channel pulse height analyzer 1420 that sorts the detected gamma signals according to their energy. FIG. 15 depicts the output of the multi-channel pulse height analyzer 1420. Additional electronic components 1425 are used to process the signals and convert them to a three-dimensional density image of the inspected object.

Detection of Scattered Gammas from the Inspected Object

During operation as shown in FIG. 14, a portion of the gammas from the source S (FIG. 15) undergo Compton scattering in the inspected object 1415 and are detected by the detector-spectrometer D (FIG. 15) after scattering through an angle θ and emerging with an energy E*.

For the sake of clarity, a discussion of the analysis of scattered gammas within the two-dimensional plane defined by the radiation source, the scattering point within the inspected object, and the detector is provided. The extension to a three-dimensional system is straightforward as previously described above. Some of the gammas from the mono-energetic source S undergo Compton scattering events within the inspected object, which is viewed by a gamma detector-spectrometer D. As described above, the locus of scattering points within the inspected object, for which the energy of detected scattered gamma photon is constant, is an isogonic surface of revolution around the axis defined by the chord joining the radiation source and the detector. In considering the broad range of scattered photon energies registered by the detector-spectrometer 1410, a multitude of virtual isogonic surfaces are created.

The gamma detector-spectrometer (D), linked to a multi-channel pulse height analyzer 1420, registers gamma photons with varying values of energy E*, scattered through a variety of angles θ, and eventually arriving at the detector D. The voltage pulse height spectrum, corresponding to an energy spectrum of detected photons, is displayed by the multi-channel pulse height analyzer 1420, as shown for example, in FIG. 15.

Analysis of Detected Signals by a Multi-Channel Pulse Height Analyzer

The output signal of the detector-spectrometer 1410 is a voltage pulse. The height of the pulse is a measure of the energy of the detected gamma photon.

Referring to FIG. 15, the detector-spectrometer 1410 registers the count rates of detected scattered gammas and sorts them into bins defined (along the horizontal axis) by an upper and lower limit of the voltage signal—representing an upper and lower limit of energy of the detected photon.

Each detected photon is registered as a counted event. Monitoring the detector signal output over any given time period enables a determination of the detected count rate (counts per second). The count rate of scattered gammas coming from any location within the inspected object 1415 is a measure of the density of material at that location—because the Compton scattering probability is directly related to the electron density of the scattering medium.

Each energy E* of scattered gammas corresponds to one channel of the multi-channel analyzer 1420, or energy bin. It displays count rates, D*, caused by detected scattered gammas having an energy that is within the bin's energy interval, denoted by ΔE(E*). The quality (spatial resolution) of the inspected object's density image derived from this measurement is influenced by the number of bins J that are selected, the value chosen for ΔE(j) that can vary with E*(j), and the overall span of energies (from $E^*_{min}$ to $E^*_{max}$) of the detected scattered gammas from within the inspected object 1415.

Either one or both of the bin's borders may be made to oscillate with time. For the former option, the voltage set-point of every odd-numbered bin border may be selected to be stationary, and every even-numbered border may be selected to vary periodically with time. The time-dependent oscillation of the bin borders can be generated, for example, by a prescribed trigonometric oscillation modulating function denoted by f'(t) on the voltage set point of the upper and lower limits (borders) of the selected pulse height channel within the multi-channel analyzer 1420.

Creation of Virtual Isogonic Arcs, Surfaces, and Inter-Arc Strips

The energy-angle relationship of gammas scattered in the Compton process causes the creation of a family of virtual isogonic surfaces of revolution around the chord that joins the source S and detector D (FIG. 15). In the simple case of a two-dimensional section through the family of isogonic surfaces, the isogonic surface becomes an isogonic curved line (arc of a circle of a specific radius) that passes through the source and the detector. For scattering points located anywhere on such an isogonic arc, the energy of scattered gammas is the same; the angle of scattering is also the same.

The average (nominal) energy of any energy bin identified in the multi-channel analyzer 1420 is associated with a particular nominal isogonic arc having a particular median radius $R_g$. The energy bin boundaries (lower energy $E_1$ and upper energy $E_2$) are associated with isogonic arc #1 with a radius of curvature $R_1$, and isogonic arc #2, with a radius of curvature $R_2$, respectively. It is noted that $R_1$ is less than $R_2$ so that $E_1 < E_2$, meaning that the photon having the higher energy is scattered through a smaller angle. The two-dimensional space between the two isogonic arcs (inter-arc strip) represents the width of the energy bin $\Delta E$.

Each energy bin of the MCA display corresponds to a specific curved isogonic inter-arc strip—whose edges are isogonic arcs representing the upper and lower boundaries of the energy bins (associated with an energy E* of scattered gammas) whose scattered gammas emerge at an angle $\theta$ corresponding to E* according to the Compton energy-angle relationship. The center line of the curved isogonic inter-arc strip is associated with the radius $R_g$ and the nominal scattering angle $\theta$. (Refer to the IO cross-section in FIG. 16, illustrating the geometric relationship among the isogonic inter-arc strip, scattering angle $\theta$, and locations of the isotopic source S, and the detector D).

The median bin-energy corresponds to the cited mid-strip isogonic line, denoted as the curvilinear x(j) axis, where j is the index number of the strip, while also serving as the index for the energy of scattered gammas E*(j). Since a single isogonic inter-arc strip corresponding with that median value of energy is addressed later in this analysis, its index j will be noted in the following discussion.

Figure 16A:
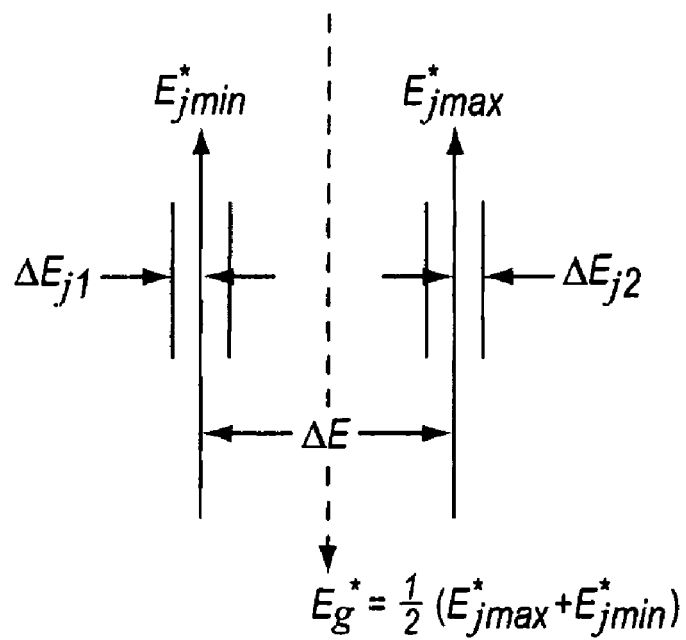
FIGS. 16A-16B illustrate the relationships among variables of a portion of an inter-arc strip in accordance with the inspection system shown in FIG. 14.
Figure 16B:
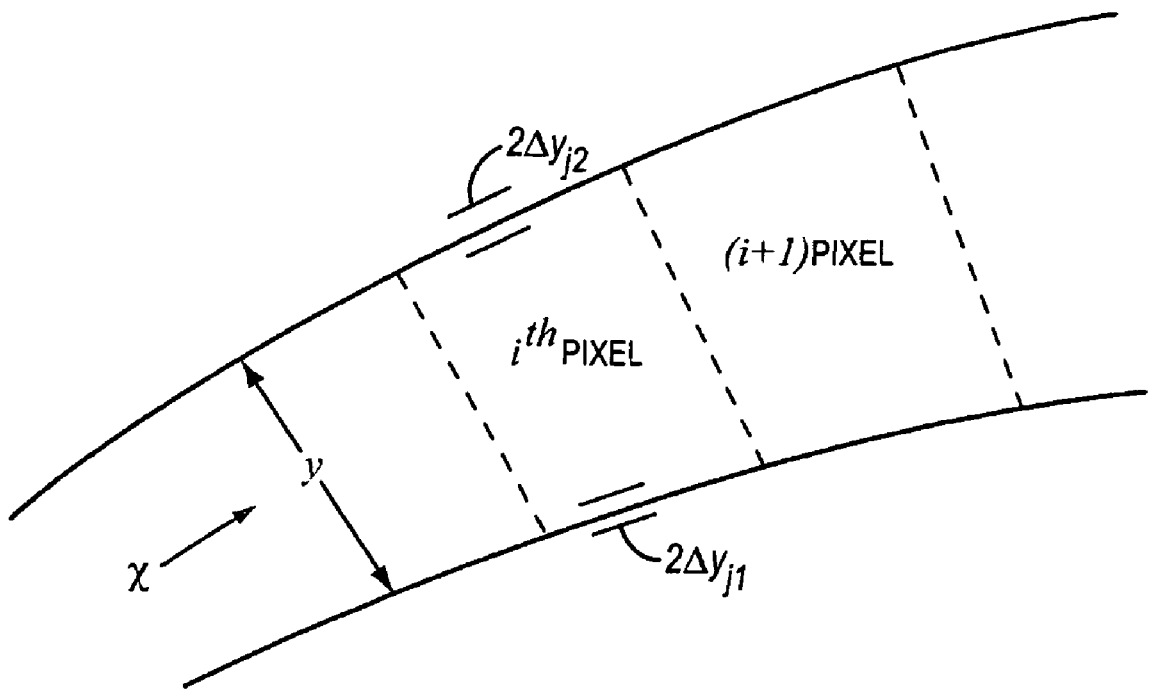

Accordingly, in the considered two-dimensional space, the voltage set points defining the energy bins also determine the boundaries of the virtual inter-arc strips within the inspected object, as shown in FIG. 16. These inter-arc strips are tapered, narrowing to a point at the source and at the detector, and being widest at the mid-point between the source and the detector.

Any fluctuation in the voltage set points of an energy bin of the MCA will produce a corresponding fluctuation in the width of the inter-arc strip (with the same frequency of oscillation as that of the energy bin boundary). However, the geometrical effect of the tapering in the inter-arc strip (narrowing to a point at the source and detector, and being widest in the center), together with the Compton energy-angle relationship for scattered gammas, causes a non-uniform fluctuation in the width of the strip in the x direction, i.e., along the length of the strip. The equation below characterizes the variation $\Delta y_1$ and $\Delta y_2$ in the strip width y at its upper and lower boundaries, respectively, with a change in the coordinate x along the strip. The $\Delta y$ variations are derived from a geometrical analysis based on FIG. 15, taking into account the Compton energy-angle scattering relationship; the cited equations are given by:

$$\Delta y_1 = \Delta E_1 L \left(\frac{Ee}{E_1^2}\right) \frac{\cos \varphi(x) - \cos \theta_1}{\sin^3 \theta_1}, \text{ with } \varphi = \theta_1 - x/R_1 \quad \text{Eq. (22)}$$

$$\Delta y_2 = \Delta E_2 L \left(\frac{Ee}{E_2^2}\right) \frac{\cos \varphi(x) - \cos \theta_2}{\sin^3 \theta_2}, \text{ with } \varphi = \theta_2 - x/R_2 \quad \text{Eq. (23)}$$

In the equations above, $\Delta E_1$ is the fluctuating amplitude of the lower limit of the energy bin, while $\Delta E_2$ is the fluctuating amplitude of the upper limit of the energy bin. The quantity Ee in Equation 22 is equal to 0.511 MeV and is the relativistic rest mass of the electron. The relationships of the variables in the above equations are shown in the accompanying illustrations of FIGS. 15 and 16.

The above equations show that the variation in the width of the inter-arc strips is dependent on the x variable along the length of the strip. That variable may be discretized into pixels of length $\Delta x$.

For this analysis, the periodic variation in the upper boundary of the energy bin voltage may be specified to be different from the periodic variation in the lower boundary of the energy bin voltage. The amplitudes of oscillation are made to be different at the boundaries of the two energy bins, but the frequency of oscillation may be the same. This arrangement results in a two-amplitude modulation of the pixels along the inter-arc strip, causing associated oscillations of the width of the inter-arc strip; according to Equations (22) and (23), these oscillations are unique for each pixel along the strip.

In this manner, by varying the two individual energy bin boundaries with a pair of unique periodic trigonometric oscillations (such as sine and cosine functions of time), the pixels within the associated virtual inter-arc strips become encoded by those unique individual oscillations.

Because the detected scattered gamma photons (in a defined energy bin) are directly related to corresponding pixels arranged along the inter-arc strips, a decoding of the pixels will allow a correlation to be made between the position of any pixel within the family of isogonic surfaces and any detected scattered photon, as previously discussed in reference to the electronic and analytic decoding process described above.

These 2-dimensional pixels become 3-dimensional voxels as the thickness of the inter-arc strip is taken into account.

In the manner described above, each voxel location (small volumetric locus around a scattering point) is correlated with the count rate of scattered gammas emerging from it—the latter being related to the density of material at that location. Based on this analysis, and following the general analytical approach described above, a straightforward analysis of the data allows reconstruction of the three-dimensional density distribution within the inspected object.

In summary, an inspection system comprising a stationary mono-energetic gamma source and single detector-spectrometer, is configured to determine the 3-dimensional density image of an inspected object—employing an electronic modulation of the energy bin boundaries within the multi-channel pulse height analyzer to encode voxels within the inspected object, and apply an analysis to reconstruct the object's 3-dimensional density image.

Analysis of Measured Data

Modulation of Voltage Set Points at Energy Bin Boundaries

Figure 17:
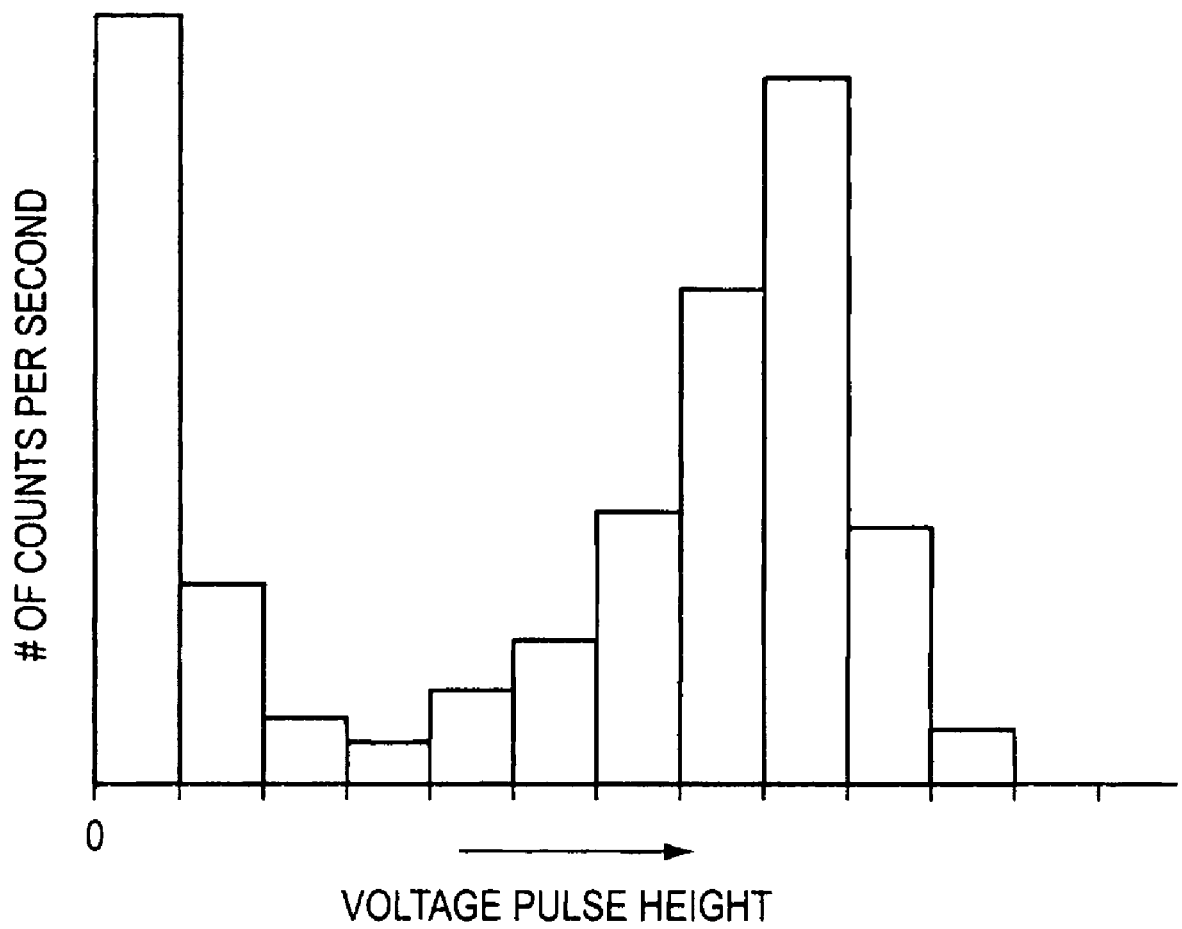
FIG. 17 is a graph showing a voltage pulse height spectrum output of a multi-channel pulse height analyzer of FIG. 14 as a function of the gamma count rate in each energy bin.

The Compton scattering law governs the relationship between the incident gamma photon energy, scattering angle, and scattered photon energy. The scattering angles determine the configuration of isogonic arcs and inter-arc strips along the isogonic surface (illustrated in FIG. 16). The moving of one or both borders of any particular energy bin causes an unambiguously defined movement of the corresponding isogonic inter-arc strip (FIG. 17).

The modulating driver function f' (the MCA's voltage supply that governs the voltage set point of each energy bin 1435) controls the temporal variation of the voltage of one or both borders of the energy bins. Resuming now the use of the energy index j for bin #j, that function, denoted as f'(ω, j, t), is shown in Eq. (24) by combining Eqs. (22) and (23). Along the isogonic inter-arc strip (containing I pixels) corresponding to energy bin #j, the individual pixels are identified by the index i. The transient variation of such a pixel is described by the function $y=f'(\omega, i, j, t)$, which corresponds to the similar $a(i, t)$-function, as described above. When the width $y(t)$ of an isogonic inter-arc strip (orthogonal to the x-axis direction along the strip) is multiplied by the selected pixel length $\Delta x$ along the x-axis (which is not time-dependent), the pixel area function $f''(t)$ can be denoted as the area function $A(i, t)$ and formulated as shown in Eq. (24). As explained below, that function describes the yield of modulated gammas having energy $E^*(j)$, that leave the $i^{th}$ pixel and are directed toward the detector D.

$$A(i, j, t) = f''(i, j, t) = [\Delta x][y(i, t)]$$
$$= C^*(i, j) + C'(i, j) \cos \omega\, t + C''(i, j) \sin \omega\, t \quad \text{Eq. (24)}$$
$$\text{with } \omega = \pi(t/T)$$

The time-average value of the pixel area A, denoted by $A(i, j, t\text{-avg.})$ is calculable from the integration over time of the above equation. The local pixel count rates $\tilde{\mathcal{D}}(i, j)$ are defined as area-specific values, i.e., pertaining to the unit area of the pixel, and are associated with the geometrical center of the pixel's time-averaged area. Therefore, such local count rate values, when multiplied with the time-average value of the $A(i, j, t)$ function, and applied to any particular pixel, will yield local (observed at the location of the scattering point) count rates from the following product:

$$\tilde{\mathcal{D}}(pix,i,j) = \tilde{\mathcal{D}}(i,j) A(i,j,t\text{-avg.}) \quad \text{Eq. (25)}$$

Superposition of a Secondary Modulation Function

The secondary modulation function $b(n, t)$—introduced above—which mimics the $A(i, j, t)$ function from Eq. (24) is shown below. The $b(n, t)$ function is a computer-generated function that is used as a multiplier of the $A(i, j, t)$ function, enabling a Fourier Transform approach to solving a set of N Linear Algebraic Equations.

$$b(n,t) = B'(n)\{\cos [\omega t]\} + B''(n)\{\sin [\omega t]\} \quad \text{Eq. (26)}$$

It is noted that any primary modulating function, such as that expressed by Eq. (24), must use the two-amplitude modulation (TAM) function, successfully employed in the embodiment described above—even when it uses two frequencies per pixel.

After the driver function $f'(j, t)$ is activated, modulating the borders of all J energy bins, all count rates from these MCA energy bins will be affected by the driver functions. The registered count rate from energy bin #j of the MCA is denoted by $D^*(j, t)$. That known temporal function which includes the contributions of all pixels along the inter-arc strip #j, is multiplied by the computer-generated function $b(n, t)$ from Eq. (26), as shown on the left-hand-side of the equation below. The right hand side of that equation sums the products of three terms: the unknown local scattered gamma count rates, the modulated area of the pixels in the isogonic strips, and the computer-generated modulation function that mimics the pixel modulation.

$$[D^*(j, t)][b(n, t)] = \sum_{i=1}^{I} [\tilde{\mathcal{D}}(i, j)][A(i, j, t)][b(n, t)] \quad \text{Eq. (27)}$$

All the terms in Eq. (27) were defined and explained earlier. The function A in the above equation is defined by Eq. (24).

Application of the Fourier Transform in Data Analysis

At this time, an integration resembling the Fourier Transform is performed, analogous to the operation described above:

$$\sigma(j, n) = \quad \text{Eq. (28)}$$
$$\int_0^{2T} [D^*(j, t)][b(n, t)] dt = \int_0^{2T} \Sigma[\tilde{\mathcal{D}}(i, j)]\{A[i, j, t]\}[b(n, t)] dt$$

Here, the term $\sigma(j, n)$ represents a definitive number which is the result of integration over time of the product of the electronically-modulated spectral signals $D^*(j, t)$, i.e., the gamma count rate from energy bin #j of detected scattered gammas and the electronically-generated $b(n, t)$ functions.

The coefficients $C^*(i)$ in Eq. (24) will vanish in the course of the above integration, because the integral of products of sine and cosine functions—from $b(n, t)$—with the cited constant argument such as $C^*$ from Eq. (22) are zero when using integration limits between 0 and 2 T. It is noted that the index n from Eq. (26) has a fixed value in a particular application of the above equation. In general terms, the integration is presented as follows, omitting the index j.

$$\sigma(n)/T = \tilde{\mathcal{D}}(1)[\underline{B'(n)\ C'(1) + B''(n)\ C''(1)}] + \quad \text{Eq. (29)}$$
$$\tilde{\mathcal{D}}(2)[\underline{B'(n)\ C'(2) + B''(n)\ C''(2)}] + \ldots \ldots +$$
$$\tilde{\mathcal{D}}(I)[\underline{B'(n)\ C'(I) + B''(n)\ C''(I)}] + \ldots = \sum_{i=1}^{I} B^*(i, n)\ \tilde{\mathcal{D}}(i)$$

Here, $B^*(i = 1, n) = [B'(n)\ C'(1) + B''(n)\ C''(1)]$,
and $B^*(i = 2, n) = [B'(n)\ C'(2) + B''(n)\ C''(2)]$.

The concise form of the integration results shown above is possible because of the rules applicable to trigonometric functions:
- All cross-products (sine×cosine) result in a zero value for the integrals.
- Similarly, products of like functions (e.g., sine×sine and cos×cos) are zero when their arguments differ due to variation of values of the angular frequencies.
- On the contrary, like products of trigonometric functions (when the same frequencies appear in both functions) result in a non-zero value of the integral equal to T, which appears in Eq. (29).

The system and device may apply the above Eq. (29) initially for n=1, using the specific function $b(1, t)$ from Eq. (26). Each underlined term in Eq. (29)—and there are I such terms, for I values of $\tilde{\mathcal{D}}(i)$—is a calculable, i.e., numerically determined coefficients—denoted for i=1 in Eq. (29) by $B^*(i,n) = B^*(1,n)$ and $B^*(2, n)$. Thus, Eq. (29) represents one equation containing 1 known coefficients $B^*(i, 1)$ and I=N unknown local $\tilde{\mathcal{D}}(i)$ values. The acquisition of other needed equations is described below.

Solution of the Set of Linear Algebraic Equations

Following execution of the above operation, an analogous integration is performed for n=2, using the corresponding function $b(2, t)$. Now, all of the 1 coefficients multiplying $\tilde{\mathcal{D}}(i)$, denoted by $B^*(i, 2)$ are also calculable, and they are different from the set of coefficients for n=1. In that way the $2^{nd}$ linear algebraic equation (LAE) is formed in the structure analogous to Eq. (29). Such an equation indicates the approach for formulating a system of linear algebraic equations by varying n from 1 to N. Following this approach, if one forms N=1 equations like Eq. (29), the operations will have generated a LAE system with N=1 independent equations, that can be solved for all I local count rates, $\mathcal{D}(i)$, in the isogonic inter-arc strip #1 under consideration, and later—in an analogous manner—local values of $\mathcal{D}(i, j)$ can be calculated for all J strips of the examined cross-section of the inspected object.

In summary, the operations leading to a solution of the equations are as follows:

After Eq. (24) is multiplied by the trigonometric, computer-generated family of functions b(n, t) and the product is integrated over time, the data analysis procedure provided in the above embodiment is applied to obtain a solution. The variations of the pixel areas along the isogonic inter-arc strip enables the generation of independent linear algebraic equations which are used to solve the local detected gamma count rates. This determination leads to the formulation of a three-dimensional image of the internals of the inspected object.

Once the local count rates $\mathcal{D}(i, j)$ for i=1 up to i=I and for j=1 up to j=J are calculated, with the analysis extended in a straight-forward manner from the two-dimensional space into the three-dimensional space, the previously described embodiment explains details of the process to obtain the three-dimensional image of the inspected object, i.e., and how to calculate local density distributions throughout the inspected object.

SUMMARY

The invention described here enables a determination of the three-dimensional density distribution within an inspected object. The invention consists of three key components: a source of mono-energetic gamma radiation, a detector in the form of a gamma spectrometer, and a multi-channel pulse height analyzer. The invention may operate without any required relative motion between the source, detector, and the inspected object (all these components may be stationary, with fixed orientation). The invention may be applied to inspect any kind of material contained in the inspected object. The voltage settings of the energy bin boundaries in the multi-channel analyzer's pulse-height spectrum may be modulated electronically to encode Compton-scattered gammas originating from voxels within the isogonic inter-arc strips in and around the inspected object. The analysis decodes the gamma spectral data to yield a three-dimensional density distribution within the inspected object. This compact inspection system may be utilized as a fully mobile unit and is flexible regarding its positioning with respect to the inspected object. Only moderate operator/technical skills and training are required to operate the device. Another beneficial feature of the invention is that the measurements can be rapidly performed because the data processing may be conducted on-line to provide immediate results of inspection of the entire inspected object. The resolution of the reconstructed images can be varied remotely by computer control, without the need to reposition or adjust hardware components.

Potential applications of the invention include, but are not limited to: 1) screening and inspections of baggage and packages at airports for the presence of contraband; 2) detection of land mines; 3) medical diagnostic imaging; and 4) a variety of industrial applications such as monitoring of material in pipes and other uses.

One having ordinary skill in the art will understand that a computer device and software may be configured to perform the above-described analysis. Accordingly, one will understand that the various configurations described herein are merely exemplary. Accordingly, although the invention has been described based upon these preferred embodiments, it would be apparent to those skilled in the art that certain modifications, variations, and alternative constructions would be apparent, while remaining within the spirit and scope of the invention. In order to determine the metes and bounds of the invention, therefore, reference should be made to the appended claims.

LIST OF NOTATIONS, FIGURE SYMBOLS, AND ACRONYMS

Figure Symbols and Acronyms are Indented

A(i, j, t)
  Time-dependent area of pixel #i in the isogonic inter-arc strip #j, that corresponds to the gamma scattering energy E*(j), which is associated with MCA pulse height energy bin #j.

A(i, j, t-avg.)
  Time-average value of the area A(i, j, t)

b(n, t)
  Computer-generated secondary modulation function, used in data processing, as described above.

B'(n) and B''(n)
  Coefficients within the function b(n, t).

B*(i, n)
  Combined coefficient, composed of coefficients B', C', or B'', C.''

C*(i, j), C*'(i, j), and C*''(i, j)
  Coefficients included in the function A(i, j, t).

D*(j, t)
  Time-dependent count rate of detected gammas scattered through the angle θ(j), and registered in bin #j of the MCA.

D
  Gamma detector-spectrometer.

$\mathcal{D}(i, j)$
  Time-independent, as yet undetermined count rate associated with pixel #i in the j-th isogonic inter-arc strip (based on the two-dimensional analysis); its value is proportional to the un-modulated local flux of scattered gammas from pixel #i, and pertains to the situation wherein A(i, j, t)=A(i, j, t-avg.).

E
  Energy of source gammas.

E*=E*(j)
  Energy of scattered gammas, registered in the j-th bin of the MCA.

$E_e$
  Relativistic rest mass of the electron (in energy units).

f'
  The time-dependent driver function that modulates the energy bin boundaries of the MCA (defined further in the paragraph above Eq. (24)).

f''
  The transient variation of the width of the isogonic inter-arc strip (defined further in the paragraph above Eq. (24)).

i, I=i(max)
  Indices along the x-axis.

j, J=j(max)
  Indices specifying the energy of scattered gammas.

MCA
  Multi-channel analyzer, which instrument displays gamma count rates D*(j, t).
n, N=n(max)
  Indices pertaining to the b(n, t) function.
R (indexed by 1, 2, or g)
  Radius of an isogonic arc; the former two are shown in FIG. 15, while the latter is the median value for these two radii.
S
  Mono-energetic gamma source.
t
  Real time, used in measurement, modulation, and Fourier Transform-like integration.
T
  Half-period of oscillation performed according to the A(i, j, t) function; the actual measurement time during the inspection is equal to a product of T with a positive integer (usually >>1).
x
  Curvilinear axis extending lengthwise along the median of an isogonic inter-arc strip.
y(i, j)
  Width of the isogonic inter-arc strip, measured perpendicular to the x-axis.
Δy
  Amplitude of the oscillating border of an inter-arc isogonic strip (indexed by 1, or 2, sometimes also by j).

What is claimed is:

1. A three-dimensional image-generating device comprising:
   an external gamma radiation source configured to irradiate an inspected object with source gamma rays to generate a three-dimensional representation of said inspected object;
   a radiation detector configured to detect Compton-scattered gamma rays scattered from within said inspected object;
   wherein said radiation detector comprises a gamma spectrometer and approximates a point detector;
   wherein said gamma spectrometer is configured to register a plurality of single detection events of said Compton-scattered gamma rays, wherein said plurality of single detection events are detected individually; and
   wherein said gamma spectrometer is configured to concurrently measure energies of Compton-scattered gamma photons associated with said detection events;
   a multi-channel pulse height analyzer coupled to said gamma spectrometer and configured to analyze voltage pulse heights representing the energies of the Compton-scattered gamma photons and sort the voltage pulse heights based upon the energies of the Compton-scattered gamma photons, into a plurality of energy bins;
   said gamma spectrometer and the multi-channel pulse-height analyzer are configured to determine a bin-average value of energy for said Compton-scattered gamma rays having a predetermined energy bin width;
   said gamma spectrometer is configured to determine values of the gamma count rate for said Compton-scattered gamma rays arriving at the detector, wherein predetermined energy bin widths are established for counted gamma rays having specific energies;
   said multi-channel pulse height analyzer is configured to assign the bin-average value of energy for each Compton-scattered photon having an energy associated with a specific isogonic arc having a specific radius;
   said multi-channel pulse height analyzer is configured to determine energy bin boundaries for each energy bin such that each energy bin is represented by a first isogonic arc having a first radius and a second isogonic arc having a second radius, wherein the first radius is less than the second radius;
   said multi-channel pulse height analyzer is configured to determine the energy bin widths and to represent a virtual two-dimensional space between the first isogonic arc and the second isogonic arc and having an inter-arc strip configuration.

2. The device as recited in claim 1, wherein voltage set points of energy bins define boundaries of the inter-arc strips within said inspected object such that the inter-arc strip is configured to taper and define a first point at the source and a second point at the radiation detector and being widest at a mid-point between the source and the radiation detector.

3. The device as recited in claim 2, further comprising:
   an electronic oscillator connected to the multi-channel pulse height analyzer voltage power supply and configured to fluctuate the voltage set points of an individual energy bin to produce a corresponding fluctuation in the width of the inter-arc strip.

4. The device as recited in claim 3, wherein a geometrical effect of the tapering of the inter-arc strip in combination with the Compton energy-angle relationship for the scattered gammas generates a non-uniform fluctuation in the width of the inter-arc strip in an x-direction along the length of the inter-arc strip.

5. The device as recited in claim 4, wherein a variation in the inter-arc strip width at an upper boundary and a lower boundary is calculated according to equations:

$$\Delta y_1 = \Delta E_1 L \left(\frac{Ee}{E_1^2}\right) \frac{\cos \varphi(x) - \cos \theta_1}{\sin^3 \theta_1}, \text{ with } \varphi = \theta_1 - x/R_1$$

$$\Delta y_2 = \Delta E_2 L \left(\frac{Ee}{E_2^2}\right) \frac{\cos \varphi(x) - \cos \theta_2}{\sin^3 \theta_2}, \text{ with } \varphi = \theta_2 - x/R_2$$

$\Delta E_1$ denotes a fluctuating amplitude of the lower limit of the energy bin;
$\Delta E_2$ denotes a fluctuating amplitude of the upper limit of the energy bin;
Ee=0.511 MeV and is the relativistic rest mass of the electron;
$R_1$ denotes a radius of curvature of the first isogonic arc; and
$R_2$ denotes a radius of curvature of the second isogonic arc.

6. The device as recited in claim 5, wherein said variation in the width of the inter-arc strip depends on an x-variable along the length of the inter-arc strip.

7. The device as recited in claim 6, wherein said energy bin boundaries comprise a lower energy boundary and an upper energy boundary; and
   a periodic variation in the upper boundary of the energy bin voltage differs in amplitude from a periodic variation in the lower boundary of the energy bin voltage.

8. The device as recited in claim 7, wherein said oscillator varies at least two individual energy bin boundaries with at least a pair of unique periodic trigonometric oscillations such that two-dimensional pixels within the associated inter-arc strip are encoded by corresponding unique individual oscillations.

9. The device as recited in claim 8, wherein rotation of the inter-arc strip around the axis defined by the chord connecting the source and the detector converts the two-dimensional pixels within the inter-arc strip into three-dimensional voxels.

10. The device as recited in claim 9, wherein the multi-channel pulse height analyzer is configured to correlate each voxel location with a count rate of the detected gammas scattered from within the voxel, and to reconstruct a three-dimensional density distribution within the inspected object.

* * * * *